United States Patent
Kwon et al.

(10) Patent No.: US 12,263,485 B2
(45) Date of Patent: *Apr. 1, 2025

(54) SUBSTRATE FOR NUCLEIC ACID AMPLIFICATION, AND METHOD FOR MANUFACTURING SAME

(71) Applicant: KOREA RESEARCH INSTITUTE OF BIOSCIENCE AND BIOTECHNOLOGY, Daejeon (KR)

(72) Inventors: Oh Seok Kwon, Daejeon (KR); Tai Hwan Ha, Daejeon (KR); Kyung Ho Kim, Daejeon (KR); Jin Yeong Kim, Daejeon (KR); Seon Joo Park, Daejeon (KR); Seong Eun Seo, Daejeon (KR)

(73) Assignee: KOREA RESEARCH INSTITUTE OF BIOSCIENCE AND BIOTECHNOLOGY, Daejeon (KR)

(*) Notice: Subject to any disclaimer, the term of this patent is extended or adjusted under 35 U.S.C. 154(b) by 1117 days.

This patent is subject to a terminal disclaimer.

(21) Appl. No.: 17/259,689

(22) PCT Filed: Jul. 12, 2019

(86) PCT No.: PCT/KR2019/008671
§ 371 (c)(1),
(2) Date: Jan. 12, 2021

(87) PCT Pub. No.: WO2020/013668
PCT Pub. Date: Jan. 16, 2020

(65) Prior Publication Data
US 2021/0229104 A1 Jul. 29, 2021

(30) Foreign Application Priority Data

Jul. 12, 2018 (KR) .................. 10-2018-0081089

(51) Int. Cl.
*B01L 7/00* (2006.01)
*B01J 19/00* (2006.01)

(52) U.S. Cl.
CPC ............. *B01L 7/52* (2013.01); *B01J 19/0046* (2013.01); *B01J 2219/0031* (2013.01);
(Continued)

(58) Field of Classification Search
None
See application file for complete search history.

(56) References Cited

U.S. PATENT DOCUMENTS

| 5,527,510 A | 6/1996 | Atwood et al. |
| 6,033,880 A | 3/2000 | Haff et al. |

(Continued)

FOREIGN PATENT DOCUMENTS

| CN | 101627044 A | 1/2010 |
| CN | 104024269 A | 9/2014 |

(Continued)

OTHER PUBLICATIONS

Li et al., "Self-Assembled N-Heterocyclic Carbene-Based Carboxymethylated Dextran Monolayers on Gold as a Tunable Platform for Designing Affinity-Capture Biosensor Surfaces," ACS Appl. Mater. Interfaces 2018, 10:17560-17570, published May 9, 2018. (Year: 2018).*

(Continued)

*Primary Examiner* — Kaijiang Zhang
(74) *Attorney, Agent, or Firm* — Hauptman Ham, LLP

(57) ABSTRACT

The present invention relates to a substrate for nucleic acid amplification, and a method for manufacturing same, the substrate for rapid and accurate PCR analysis comprising: a transparent substrate; a micro-patterned metal layer formed on the transparent substrate; an N-heterocyclic carbene compound having one end annealed to the surface of the (Continued)

micro-patterned metal layer; and a primer immobilized on the other end of the N-heterocyclic carbene compound.

16 Claims, 23 Drawing Sheets

Specification includes a Sequence Listing.

(52) U.S. Cl.
CPC .............. *B01J 2219/00497* (2013.01); *B01J 2219/00722* (2013.01); *B01L 2200/0663* (2013.01); *B01L 2300/0819* (2013.01); *B01L 2300/123* (2013.01); *B01L 2300/16* (2013.01); *B01L 2300/1861* (2013.01)

(56) References Cited

U.S. PATENT DOCUMENTS

| | | |
|---|---|---|
| 7,833,701 B2 | 11/2010 | Oshima |
| 8,663,976 B2 | 3/2014 | Chung et al. |
| 8,691,560 B2 | 4/2014 | Oshima |
| 10,766,034 B2 | 9/2020 | Lee et al. |
| 2004/0259083 A1 | 12/2004 | Oshima |
| 2010/0286113 A1 | 11/2010 | Saxty et al. |
| 2011/0071048 A1 | 3/2011 | Oshima |
| 2012/0052531 A1 | 3/2012 | Chung et al. |
| 2013/0026453 A1 | 1/2013 | Kunze et al. |
| 2013/0122489 A1 | 5/2013 | Stupi et al. |
| 2015/0176074 A1 | 6/2015 | Stupi et al. |
| 2016/0355484 A1 | 12/2016 | Johnson et al. |
| 2016/0369336 A1 | 12/2016 | Stupi et al. |
| 2017/0107516 A1 | 4/2017 | Veige et al. |
| 2017/0327886 A1 | 11/2017 | Stupi et al. |
| 2018/0080064 A1 | 3/2018 | Lee et al. |
| 2018/0201968 A1 | 7/2018 | Chen et al. |
| 2018/0236451 A1 | 8/2018 | Lee et al. |
| 2019/0127790 A1 | 5/2019 | Stupi et al. |

FOREIGN PATENT DOCUMENTS

| | | |
|---|---|---|
| CN | 105518685 A | 4/2016 |
| JP | 2001-299346 A | 10/2001 |
| JP | 2010-41985 A | 2/2010 |
| KR | 10-2008-0089834 A | 10/2008 |
| KR | 10-2009-0012282 A | 2/2009 |
| KR | 10-2012-0020528 A | 3/2012 |
| KR | 10-2012-0129905 A | 11/2012 |
| KR | 10-2017-0106995 A | 9/2017 |
| KR | 10-2018-0034579 A | 4/2018 |
| WO | 2013/105679 A1 | 7/2013 |
| WO | 2020/013664 A1 | 1/2020 |

OTHER PUBLICATIONS

Wang et al., "DNA microarray fabricated on poly(acrylic acid) brushes-coated porous silicon by in situ rolling circle amplification," Analyst 2012, 137:4539-4545. (Year: 2012).*

Wang et al., "Peptide-decorated gold nanoparticles via strain-promoted azide-alkyne cycloaddition and post assembly deprotection," RSC Adv. 2014, 4:43087-43091. (Year: 2014).*

Zhijun Li et al., "Self-Assembled N-Heterocyclic Carbene-Based Carboxymethylated Dextran Monolayers on Gold as a Tunable Platform for Designing Affinity-Capture Biosensor Surfaces", Applied Materials & Interfaces, Oct. 2018, pp. 17560-17570, vol. 10.

Xiaoxiao Wang et al., "Peptide-decorated gold nanoparticles via strainpromoted azide-alkyne cycloaddition and post assembly deprotection", RSC Advances, 2014, pp. 43087-43091, vol. 4.

International Search Report dated Oct. 18, 2019, in connection with corresponding International Patent Application No. PCT/KR2019/008671.

Written Opinion dated Oct. 18, 2019, in connection with corresponding International Patent Application No. PCT/ KR2019/008671.

Cathleen M. Crudden et al., "Ultra stable self-assembled monolayers of N-heterocyclic carbenes on gold", Nature Chemistry, Mar. 23, 2014, pp. 409-414, vol. 6.

Ozden Karaca et al., "Characterization of Hydrophilic Gold(I) N-Heterocyclic Carbene (NHC) Complexes as Potent TrxR Inhibitors Using Biochemical and Mass Spectrometric Approaches", Inorganic Chemistry, 2017, pp. 14237-14250, vol. 56.

Extended European Search Report issued on Jul. 12, 2021, corresponding to European Application No. 19834182.8.

Zhijun Li et al, Self-Assembled N-heterocyclic Carbene-Based Carboxymethylated Dextran Monolayers on Gold as a Tunable Platform for Designing Affinity Capture Biosensor Surfaces, ACS Applied Materials & Interfaces, May 9, 2018, 35 Pages.

Korean Office Action issued on Mar. 26, 2021, in connection with the Korean Patent Application No. 10-2019-0084698.

Korean Office Action issued on Mar. 26, 2021, in connection with the Korean Patent Application No. 10-2019-0084699.

Office Action issued on Apr. 8, 2024 for U.S. Appl. No. 17/259,821 (32 pages).

Office Action issued on Apr. 28, 2024 for corresponding Chinese Patent Application No. 201980046390.7 along with partial English translation (7 pages).

* cited by examiner (A) DOUBLE EXPOSURE PHOTORESIST STATE AFTER DOUBLE EXPOSURE (B) STATE AFTER GOLD DEPOSITION

SINGLE EXPOSURE PHOTORESIST STATE AFTER SINGLE EXPOSURE

SUBSTRATE FOR NUCLEIC ACID AMPLIFICATION, AND METHOD FOR MANUFACTURING SAME

CROSS-REFERENCE TO RELATED APPLICATION

The present application is a national stage filing under 35 U.S.C § 371 of PCT application number PCT/KR2019/008671 filed on Jul. 12, 2019 which is based upon and claims the benefit of priorities to Korean Patent Application No. 10-2018-0081089, filed on Jul. 12, 2018, in the Korean Intellectual Property Office, which are incorporated herein in their entireties by reference.

TECHNICAL FIELD

The present invention relates to a substrate for nucleic acid amplification, and a method for manufacturing same.

BACKGROUND ART

A polymerase chain reaction (PCR) method is technique allowing amplification of a specific region of DNA or RNA to a large amount in vitro. A PCR machine using such technique is used for the amplification of a small amount of DNA included in blood in hospitals, research centers, etc., and the PCR machine is also used for diagnosing various diseases including malaria, tuberculosis, hepatitis, etc.

PCR is conducted through one cycle of three steps including denaturation, annealing and elongation, and the rapid rise and drop of temperature in line with the temperature suitable for each step is very important for reducing PCR reaction time. That is, PCR requires the instant shift of the temperature in line with the temperature set for each step, but if time delay is generated during the process for changing the temperature to the preset temperature, a reaction rate is degraded, total PCR reaction time increases, and there are problems of arising unnecessary reactions to produce by-products. Particularly, the decrease of the PCR time enables prompt diagnosis on the spot of infectious diseases which are recently spread rapidly, and plays an important role of serving early disinfection.

However, the conventionally used PCR machine uses electrical energy as a thermal energy source, and a long time of about 1 hour or more is required for completing nucleic acid amplification reaction, and since accessories including a heating instrument and a heat sink are necessary, there are problems of inconvenience in that the apparatuses occupy much space. Accordingly, the application on the spot requiring the prompt diagnosis of diseases is a little bit inconvenient. In addition, Korean Laid-open Patent Publication No. 2017-0106995 discloses a light energy-based PCR system, but there are problems in that PCR is performed in a liquid phase, multiple diagnoses in one chamber is impossible, and the recovery of a used primer is impossible. Particularly, due to a high price, the enlargement of the apparatus and long detection time (1 hour or more), the conventional PCR machine is inconvenient to carry, and immediate diagnosis on the spot is limited.

Therefore, research on PCR for stable, rapid and precise diagnosis irrespective of high temperature and rapid change of the temperature, is steadily being conducted.

PRIOR ART DOCUMENT (Patent Document 1) Korean Laid-open Patent Publication No. 2017-0106995

DISCLOSURE OF THE INVENTION

Technical Problem

The present invention has been devised to solve the above-described problems and provides a substrate for nucleic acid amplification serving stable at high temperature and rapid multiple PCR reactions by immobilizing a primer on the surface of a micro-patterned metal layer using an N-heterocyclic carbene compound as a linker, while amplifying nucleic acid using thermal energy generated by irradiating light energy. Further, according to the micro-patterning of the metal layer, PCR reaction with even quicker and even higher accuracy may be performed.

Technical Solution

The present invention provides a substrate for nucleic acid amplification including a transparent matrix, a micro-patterned metal layer formed on the transparent matrix, an N-heterocyclic carbene compound having one end bonded to the surface of the micro-patterned metal layer and a primer immobilized on the other end of the N-heterocyclic carbene compound.

In addition, the present invention provides a method for manufacturing a substrate for nucleic acid amplification, including forming a micro-patterned metal layer on a transparent matrix, introducing one end of an N-heterocyclic carbene compound onto the surface of the micro-patterned metal layer, and immobilizing a primer on the other end of the N-heterocyclic carbene compound.

Advantageous Effects

In case of using the substrate for nucleic acid amplification of the present invention in polymerase chain reaction (PCR), by immobilizing a primer after annealing an N-heterocyclic carbene compound on the surface (solid phase) of a micro-patterned metal layer, PCR reaction may be more stable at high temperature and completed in a very short time when compared with a case of using a linker by the bond between a metal and thiol (—SH).

In addition, according to the micro-patterning of the metal layer, and according to vortex phenomenon by heat transfer generated by the temperature difference between micro-patterned parts and non-micro-patterned parts, the temperature control of the micro-patterned metal layer may be achieved even faster, and thus, PCR reaction time may be further reduced.

Further, according to the PCR reaction on a solid phase (transparent matrix/micro-patterned metal layer), the recovery of a primer after the PCR reaction is easy, and various types of primers could be immobilized on the N-heterocyclic carbene compound at the surface of each micro-patterned metal layer, and thus, the simultaneous amplification of diverse nucleic acids is possible, and there are advantages of performing multiple PCR reactions and finally, serving more precise diagnosis.

BRIEF DESCRIPTION OF THE INVENTION

EXPLANATION ON SYMBOLS

Figure 1:
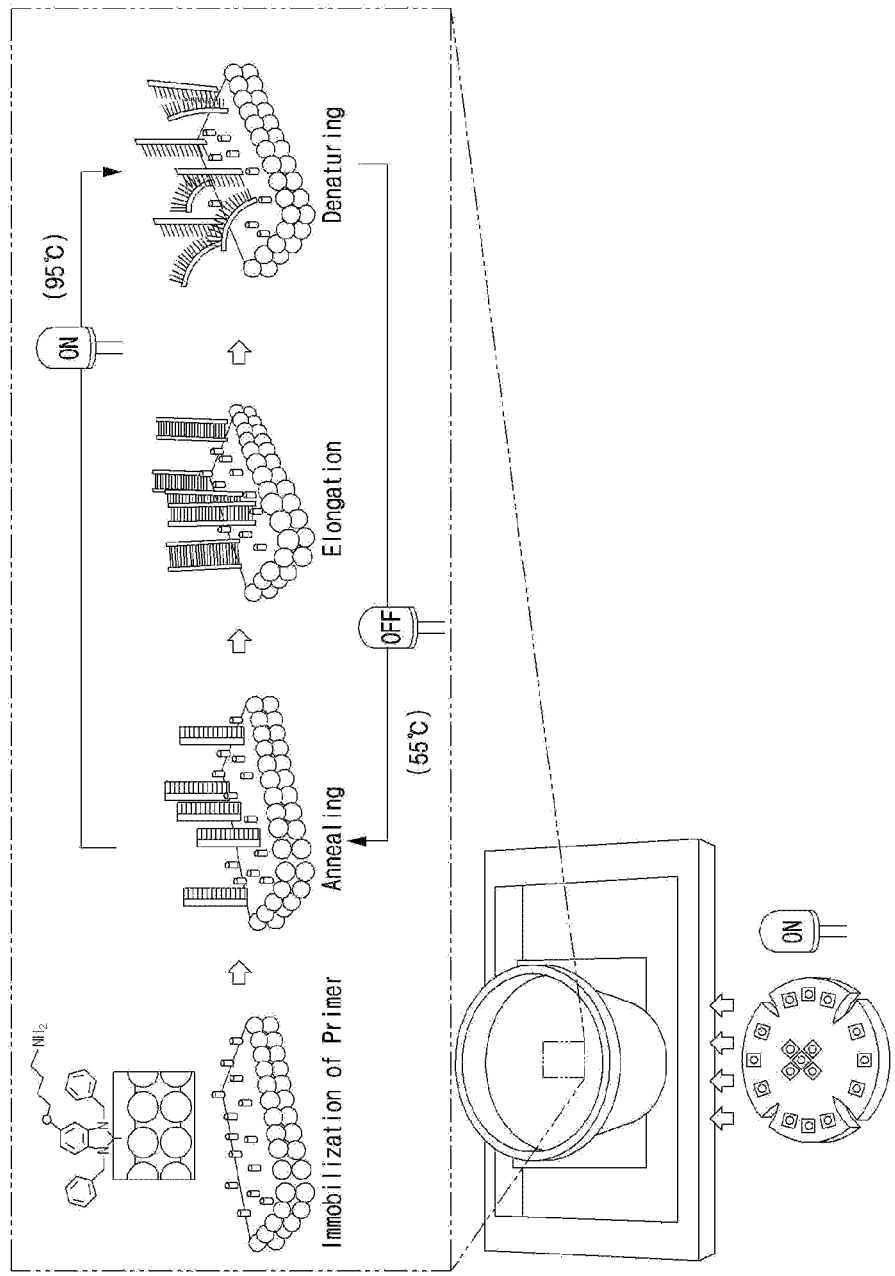
FIG. 1 is a diagram schematically showing a series of light-based PCR reaction using the substrate for nucleic acid amplification of the present invention.

10: transparent matrix
20: metal layer
30: thermocouple

MODE FOR CARRYING OUT THE INVENTION

Hereinafter, the present invention will be explained in detail.

The present invention provides a substrate for nucleic acid amplification including: a transparent matrix; a micro-patterned metal layer formed on the transparent matrix; an N-heterocyclic carbene compound having one end bonded to the surface of the micro-patterned metal layer; and a primer immobilized on the other end of the N-heterocyclic carbene compound.

The substrate for nucleic acid amplification may be used in polymerase chain reaction (PCR) which is molecular biological technique for duplicating and amplifying a desired segment of DNA or RNA.

The first step of PCR is a step for denaturing DNA (or RNA). Two strands of DNA may be separated by heating, and each separated DNA plays the role of a template. The denaturation temperature is generally 90° C. to 96° C., but is changed according to the amount of bases G+C in DNA and the length of DNA. The second step of PCR is a step of annealing. In this step, two types of primers are annealed to each complementary template DNA. The annealing temperature is an important factor for determining the accuracy of reaction, and if the temperature is too high, the primer may be annealed on DNA too weakly, and the product of amplified DNA may be very small. If the temperature is too low, the primer may be non-specifically annealed, and undesired DNA may be amplified. General annealing temperature is 50° C. to 65° C. The third step of PCR is a step of elongation. In this step, DNA polymerase resistant to heat produces new DNA in template DNA. In this case, the elongation temperature is 70° C. to 75° C. As described above, there are a series of three steps in the PCR reaction, and if the three steps are set to 1 cycle, the PCR reaction is performed by about 30 to 40 cycles.

The substrate for nucleic acid amplification may be used in light-based PCR using thermal energy produced by the irradiation of light energy during the above-described PCR.

The light-based PCR may use plasmonic photothermal conversion by the interaction of photons, electrons and phonons at the surface of a metal. Particularly, if photons reach the surface of a metal layer from an excited energy source, light-absorption occurs, and electrons around the surface are excited to a higher state to form electrons of high temperature. According to the rapid diffusion and uniform distribution of such electrons of high temperature to the whole metal layer, a metal layer of high temperature may heat surrounding solutions. In addition, the electrons of high temperature may be cooled again by energy exchange with lattice phonons.

The temperature of the metal layer in which plasmons are excited as described above may be elevated to maximum 500° C., and a PCR specimen solution around the metal layer may be heated to 150° C. or more in a short time.

The transparent matrix may be manufactured so that light irradiated from a light source positioned under a counter surface to the micro-patterned metal layer formed is transferred to the micro-patterned metal layer without loss, and adhesiveness with the micro-patterned metal layer is excellent.

The light source is not limited only if generating ultraviolet rays, visible rays or infrared rays, and may use a halogen lamp, an LED lamp, a fluorescent lamp, an incandescent lamp, an arc source lamp, an infrared lamp, an HMI lamp, a UV lamp, etc., preferably, an LED lamp considering power efficiency and economic feasibility.

The transparent matrix may be formed using a transparent material so as to transmit light irradiated, and may be formed using a material which is hardly deformed by light or heat. Preferably, a glass matrix, a plastic matrix, a silicon matrix, etc., may be used, but is not limited thereto.

The transparent matrix has a constant thickness, and the thickness of the transparent matrix may be from 0.1 mm to 10 mm, preferably, from 0.5 mm to 5 mm, more preferably, from 0.5 mm to 1.5 mm. If the thickness of the transparent matrix satisfies the above-described range, thermal energy by light energy irradiated from a light source may be efficiently transferred, and a PCR reaction cycle may be optimized.

The transparent matrix may include a two-dimensional matrix of a planar type; a three-dimensional matrix selected from a spherical type, a hemispherical type, a polyhedral type, a polyprism type, or a cylindrical type; or a mixture type thereof. For example, as in FIG. 18 and FIG. 19, the transparent matrix may include a matrix of a mixture type of a three-dimensional matrix in which at least one partial surface of the polyhedral type a matrix includes hemispherical type matrix.

In case where the transparent matrix includes the three-dimensional matrix as described above, PCR reaction may be performed at many faces, and there are advantages in that diverse nucleic acids may be amplified simultaneously, and multiple diagnosis may be possible.

The substrate for nucleic acid amplification may utilize a micro-patterned metal layer for utilizing thermal energy by the irradiation of light energy. In case of using the micro-patterned metal layer, the temperature may be instantly elevated to maximum 500° C., and the temperature change in the temperature range (from about 50° C. to 95° C.) of the PCR cycle may be promptly conducted.

The metal layer may include a metal thin film.

The metal layer may further include a metal mesh. In case where the metal layer further includes a metal mesh, the metal mesh may be formed first on the transparent matrix, and then the metal layer may be formed on the metal mesh. In case where the metal layer further includes the metal mesh, prompt heating and cooling may be possible when compared with a case of using only a metal layer, the temperature change of a PCR cycle may be promptly conducted, and more efficient PCR reaction may be performed.

Figure 26:
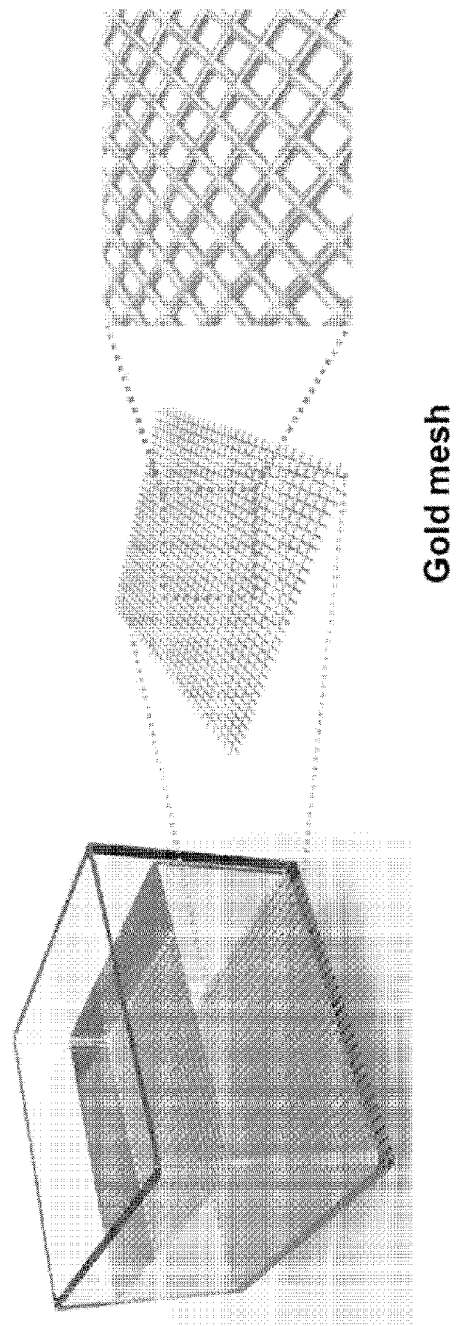
FIG. 26 is a diagram showing a transparent matrix including a gold mesh according to an embodiment of the present invention.
Figure 27:
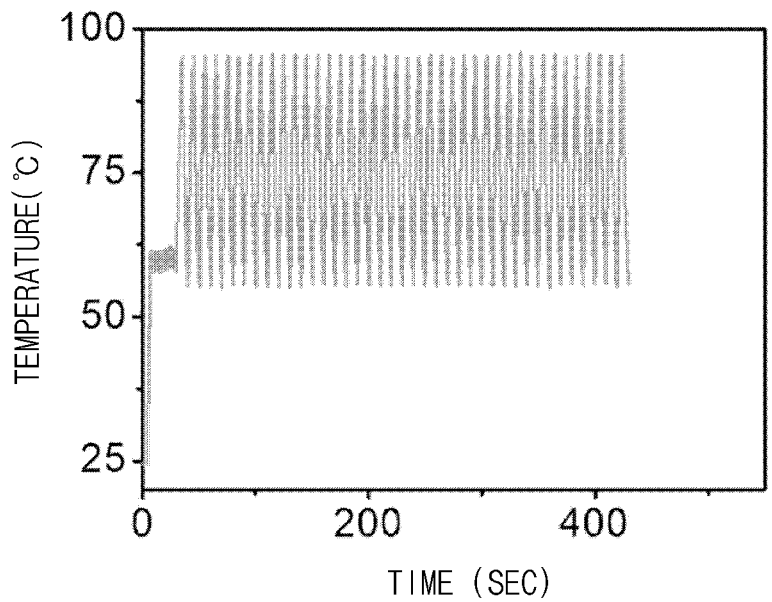
FIG. 27 is a diagram showing time required for performing 40 cycles of PCR reaction in case of including a metal mesh as in FIG. 26.

As in FIG. 26, if a metal mesh is provided, the temperature change in the temperature range (from about 50° C. to 95° C.) of the PCR cycle may be promptly conducted, and as in FIG. 27, it could be confirmed that the time required for performing 40 cycles of the PCR reaction is significantly short and about 7 minutes.

In case where the metal layer is formed on the transparent matrix, the metal layer may be formed on at least one face of the transparent matrix. In this case, the metal layer may be formed on the whole face of the at least one face of the transparent matrix, or may be partially formed on the at least one face of the transparent matrix. That is, on the transparent matrix, one metal layer may be formed, or multiple metal layers may be formed.

The metal mesh may have a two-dimensional or three-dimensional structure, and in this case, the mesh may include a polygonal pattern including a triangle, a tetragon, a pentagon and hexagon, or a circular pattern, but is not limited thereto.

In case where the mesh includes a polygonal pattern, the length of one side of the mesh may be from 50 to 200 μm, and in case where the mesh includes a circular pattern, the diameter of the mesh may be from 50 to 200 μm. In addition, the spacing of the mesh may be from 1 to 5 μm, particularly, 1 to 2 μm. The thickness of the metal mesh may be from 10 nm to 200 nm, particularly, from 100 to 200 nm. In case where the thickness of the metal mesh and the size of the mesh satisfy the above-described ranges, prompt heating and cooling may become possible, and the temperature change of the PCR cycle may be promptly conducted when compared with a case of using only a metal layer.

Figure 13:
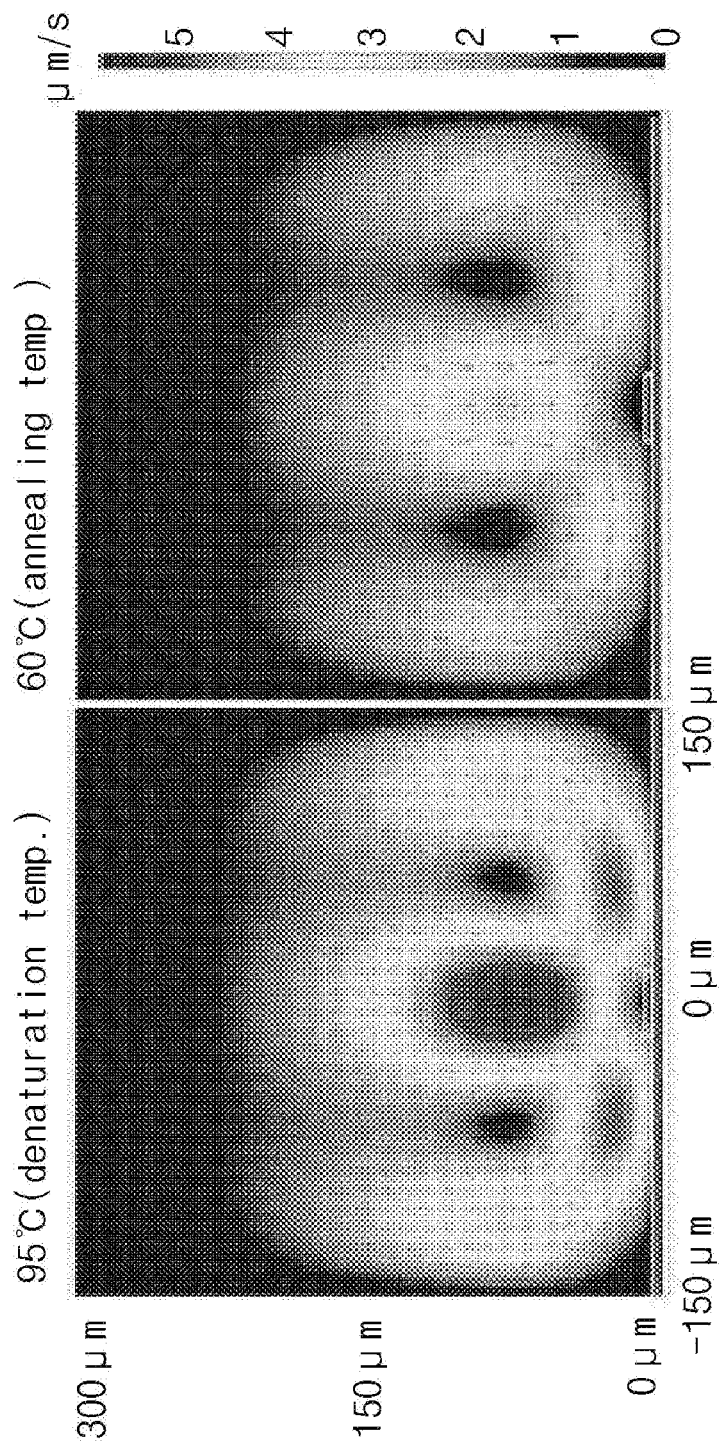
FIG. 13 is a diagram showing vortex phenomenon according to heat transfer at the surface of the micro-patterned gold (Au) layer according to an embodiment of the present invention.
Figure 14:
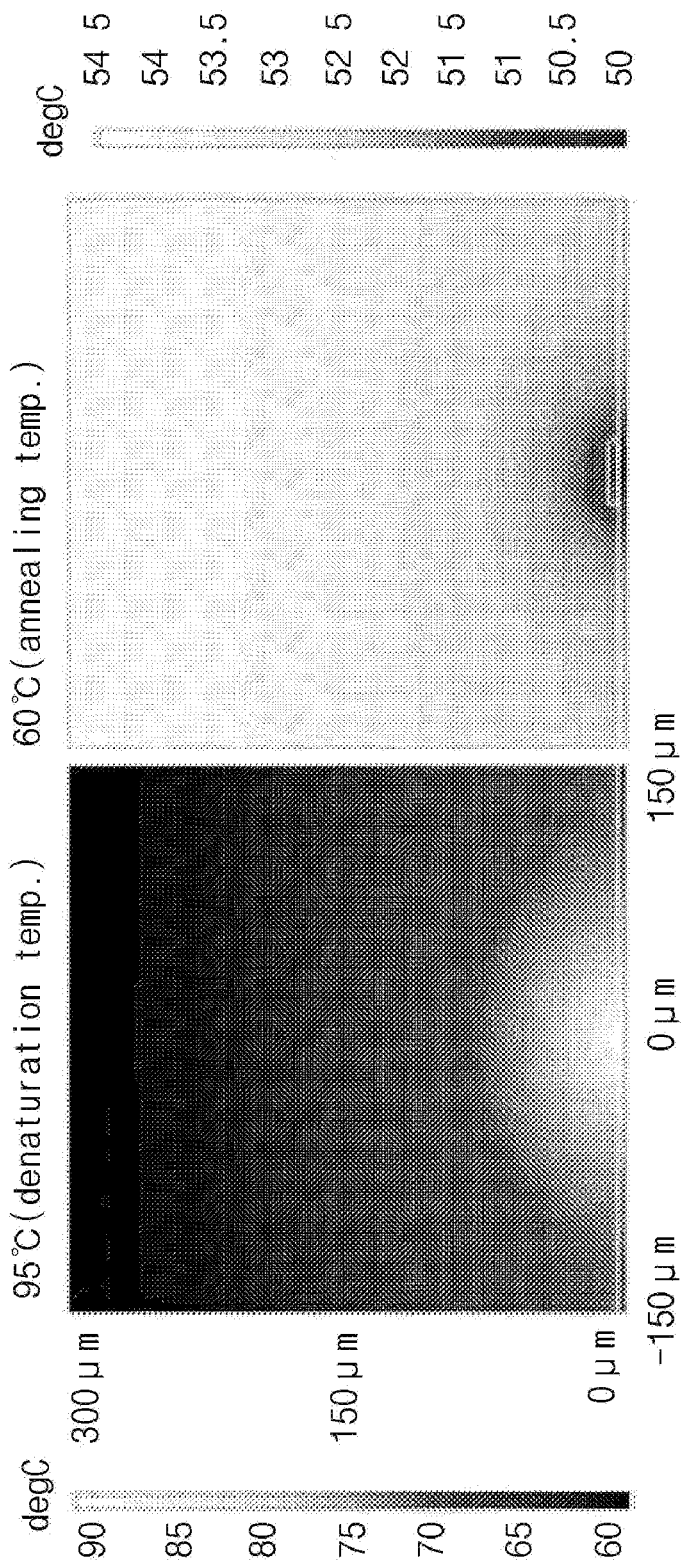
FIG. 14 is a diagram showing temperature distribution at the surface of the micro-patterned gold (Au) layer according to an embodiment of the present invention.
Figure 15:
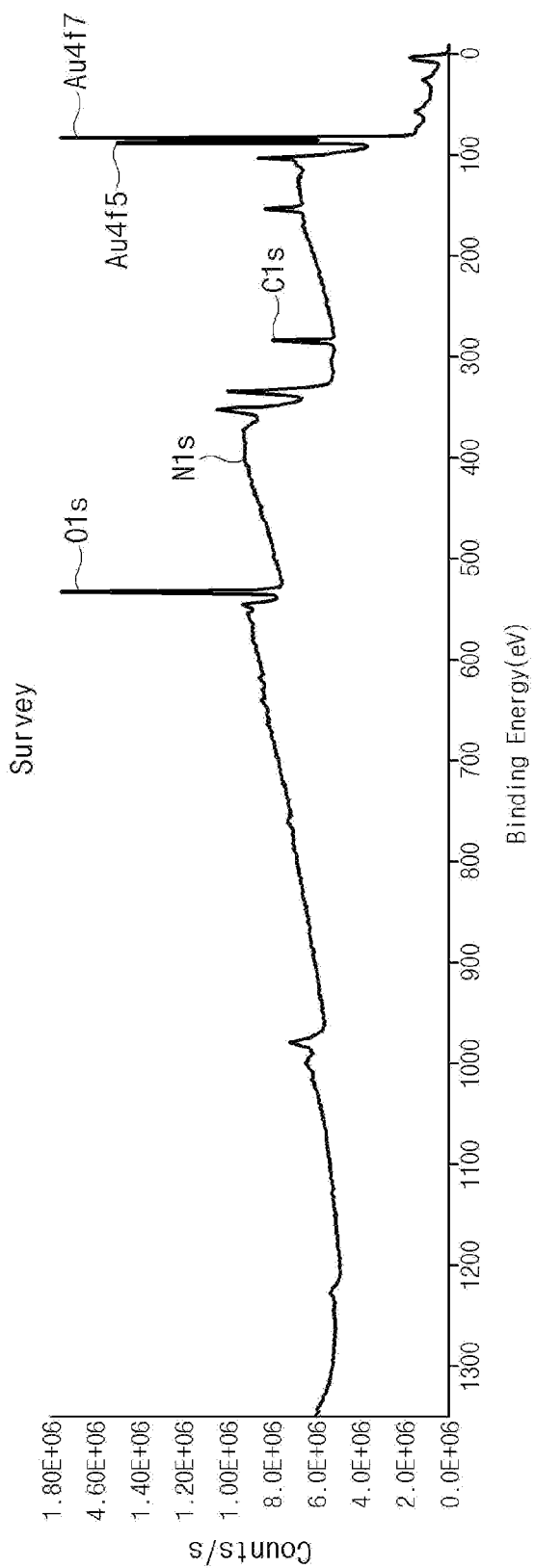
FIG. 15 is a diagram showing XPS elemental analysis results of a gold (Au) layer on which N-heterocyclic carbene compound 4 bonded according to Example 1 of the present invention.

Particularly, in case of micro-patterning the metal layer, the temperature of the micro-patterned part may be rapidly elevated, and the temperature between non-patterned parts in the pattern may be relatively lowered, and vortex phenomenon may be generated due to a temperature difference. In this case, according to the spacing of the micro-pattern, the size and shape of the pattern, the degree of vortex phenomenon due to heat transfer is determined. The vortex phenomenon according to the heat transfer generated at the surface of the micro-patterned gold (Au) layer according to an embodiment of the present invention is shown in FIG. 13.

Figure 3:
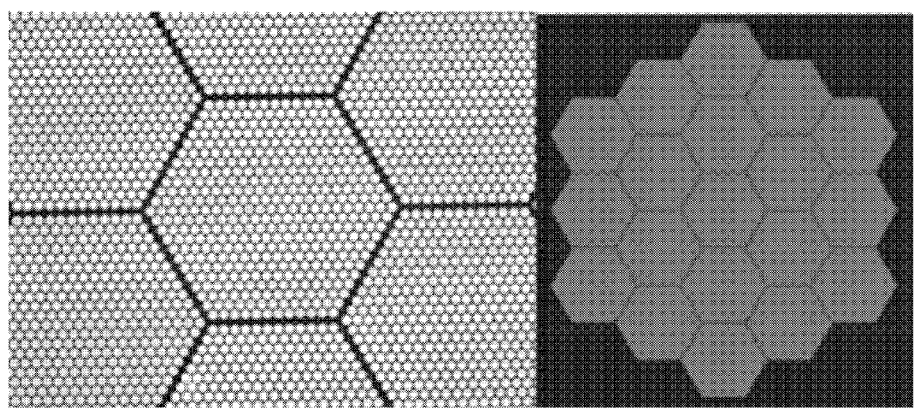
FIG. 3 is a diagram showing a honeycomb pattern according to an embodiment of the present invention.
Figure 4:
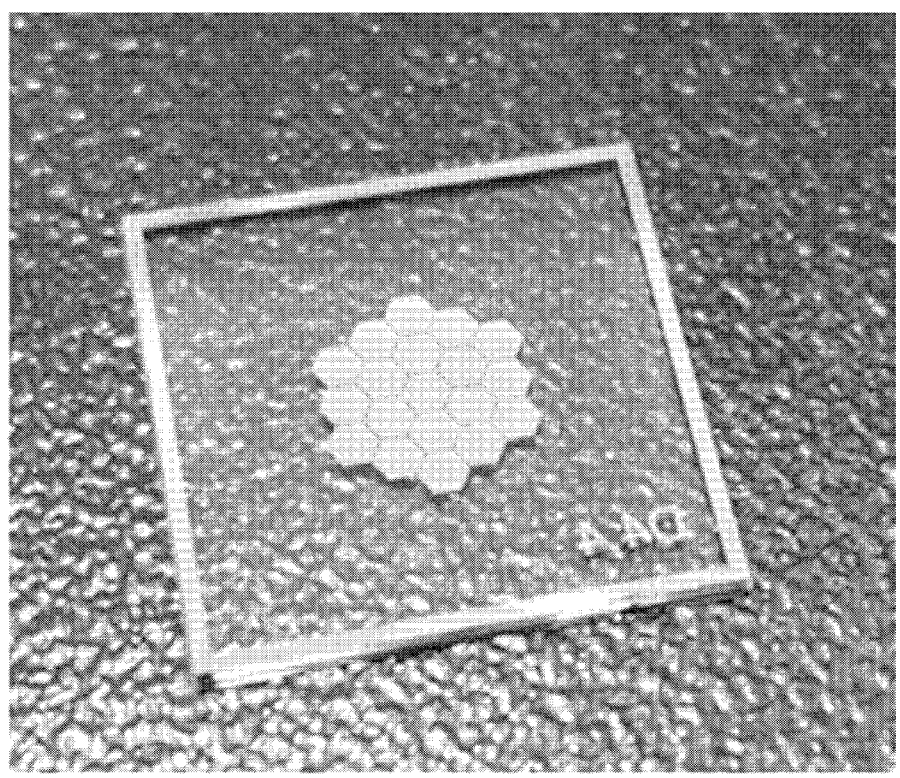
FIG. 4 is a diagram showing a micro-patterned gold (Au) layer formed into a honeycomb pattern on a transparent matrix included in the substrate for nucleic acid amplification of the present invention.

The micro-pattern may have a circle or a polygonal shape such as a triangle, a tetragon, a pentagon and hexagon. Preferably, the micro-pattern may have a honeycomb pattern as shown in FIG. 3 and FIG. 4.

The size of the micro-pattern may be such that an average diameter or the radius of a circumscribed circle is from 1 μm to 20 μm. For example, in case where the micro-pattern is a circle, the average diameter, or in case where the micro-pattern is a polygonal shape, the radius of a circumscribed circle may be from 1 μm to 20 μm.

The average spacing of the micro-pattern may be from 3 μm to 5 μm.

The metal layer may include any one selected from the group consisting of copper (Cu), silver (Ag), gold (Au), palladium (Pd), platinum (Pt), rhodium (Rh) and combinations thereof (for example, bimetallic nanoparticles). Preferably, gold (Au) which has excellent bonding properties with an N-heterocyclic carbene compound and stability, may be included.

The method of coating the micro-patterned metal layer on one side of the transparent matrix may use any coating or deposition technique without limitation, and the transparent matrix may be formed into a uniform thickness by a method of chemical vapor deposition (CVD), physical vapor deposition (PVD), thermal evaporation deposition, sputtering deposition or atomic layer deposition (ALD).

As a method for micro-patterning the metal layer, any methods may be used as long as it is patterning technique, and among the methods, double exposure lithography, nano imprint lithography (NIL), electron beam lithography (EBL), focused ion beam (FIB), soft lithography (SL), self-assembly of block copolymers, etc., may be used for patterning the metal layer.

Figure 5:
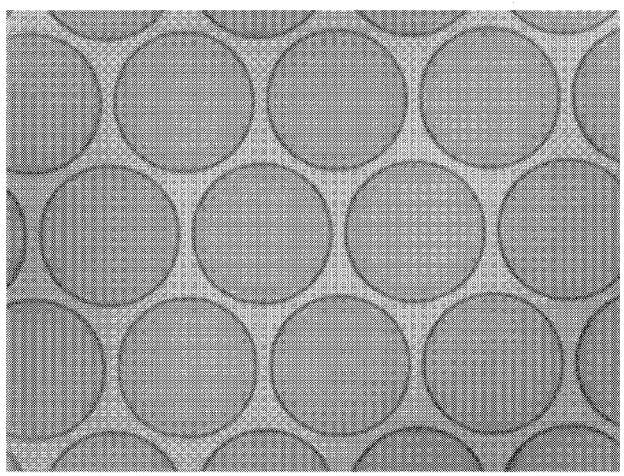
FIG. 5(A) shows an exposed pattern of a photoresist by a double exposure lithography method according to an embodiment of the present invention.
FIG. 5(B) is shows an exposed pattern of a photoresist by a double exposure lithography method after depositing a gold (Au) layer.
Figure 5:
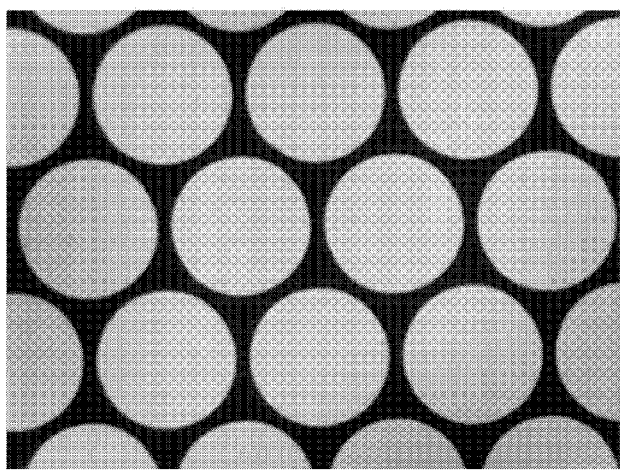
Figure 6:
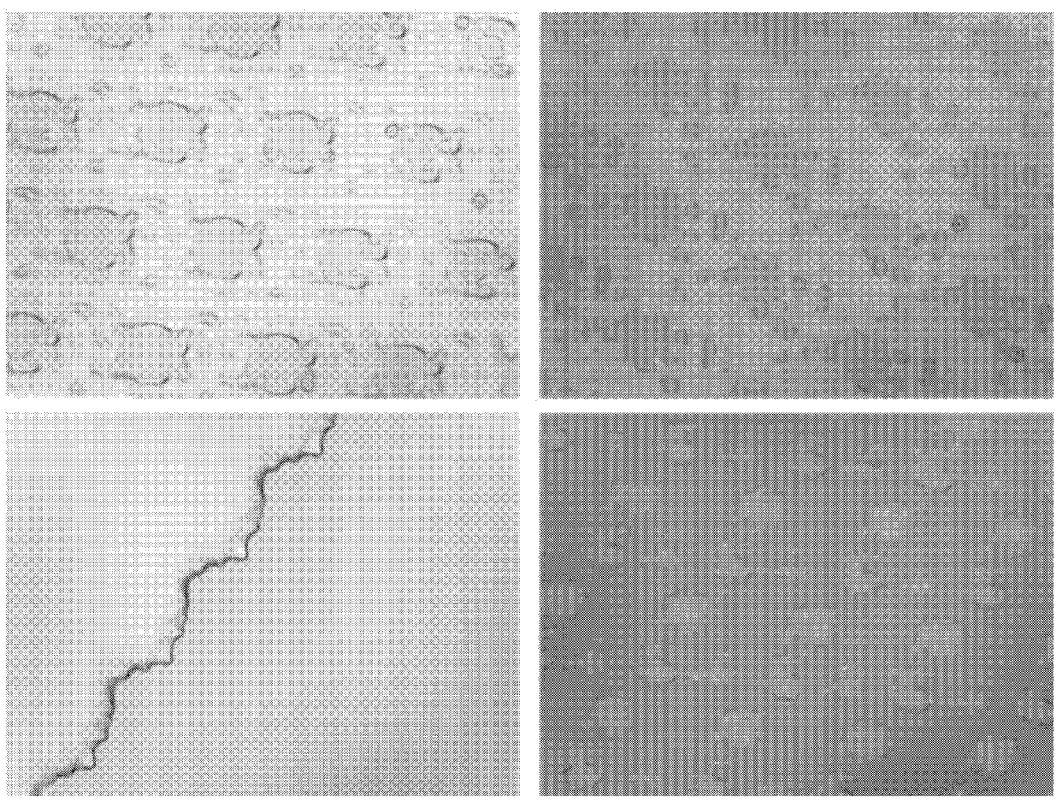
FIG. 6 shows an exposed pattern of a photoresist by the conventional single exposure lithography method.

Preferably, the micro-patterning into a more uniform and clearer shape may be achieved through patterning by the double exposure lithography rather than the conventional single exposure lithography. In addition, as shown in FIG. 5 and FIG. 6, the patterning of the micro-pattern with the spacing of from 3 μm to 5 μm is difficult by the single exposure lithography, but the patterning of the micro-pattern with the spacing of from 3 μm to 5 μm is possible by the double exposure lithography.

The thickness of the micro-patterned metal layer may be from 10 nm to 200 nm. If the thickness of the micro-patterned metal layer is greater than the range, there are problems in that the metal layer may be damaged during the step of immobilizing a linker, or a linker may be non-uniformly formed.

As a linker for immobilizing the primer on the surface of the micro-patterned metal layer, an N-heterocyclic carbene compound may be used. The N-heterocyclic carbene compound may be introduced onto the surface of the micro-patterned metal layer through a metal-carbene bond.

Particularly, in case of a linker having a thiol (—SH) group used in the conventional solid phase PCR, there are problems of degrading the reproducibility of PCR reaction results due to the unstability (cleaving of a metal-sulfur bond) of a metal-sulfur bond at high temperature (about 90° C.). In contrast, in case of using the N-heterocyclic carbene compound as a linker for immobilizing the primer onto the micro-patterned metal layer, though the surface temperature of the micro-patterned metal layer temporarily rises to maximum 500° C. by a light source, stability at high temperature may be achieved due to a metal-carbene bond, and the application thereof to a PCR machine using light energy is possible.

The N-heterocyclic carbene compound may be represented by Chemical Formula 1 or 2 below.

[Chemical Formula 1]

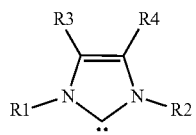

[Chemical Formula 2]

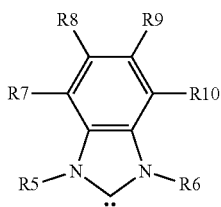

In Chemical Formulae 1 and 2,

R1, R2, R5 and R6 are the same or different, and are each independently hydrogen, an alkyl group of 1 to 20 carbon atoms, a cycloalkyl group of 3 to 20 carbon atoms, an aryl group of 6 to 30 carbon atoms or a heteroaryl group of 2 to 30 carbon atoms, R3, R4, R7, R8, R9 and R10 are the same or different, and are each independently hydrogen, an alkyl group of 1 to 20 carbon atoms, a cycloalkyl group of 3 to 20 carbon atoms, an aryl group of 6 to 30 carbon atoms, a heteroaryl group of 2 to 30 carbon atoms or a structure represented by Chemical Formula 3 below, where adjacent more substituents among R7 to R10 are bonded to form a hydrocarbon ring, at least one of R3 and R4 is the structure represented by Chemical Formula 3 below, and at least one of R7 to R10 is substituted with the structure represented by Chemical Formula 3 below, or in case where adjacent two or more substituents among R7 to R10 are bonded to form a hydrocarbon ring, at least one of carbon atoms forming the hydrocarbon ring is substituted with the structure represented by Chemical Formula 3 below,

[Chemical Formula 3]

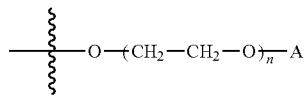

in Chemical Formula 3, n is a repeating number of a unit in parenthesis and an integer of 1 to 30, and A is a nitrogen (N)-containing alkyl group of 1 to 20 carbon atoms or a nitrogen (N)-containing heteroaryl group of 2 to 30 carbon atoms.

R1, R2, R5 and R6 may be the same or different, and may be each independently hydrogen, an alkyl group of 1 to 20 carbon atoms or an aryl group of 6 to 30 carbon atoms.

R1, R2, R5 and R6 may be the same or different, and may be each independently hydrogen, an alkyl group of 1 to 10 carbon atoms or an aryl group of 6 to 10 carbon atoms.

R1, R2, R5 and R6 may be the same or different, and may be each independently hydrogen or an alkyl group of 1 to 10 carbon atoms.

R1, R2, R5 and R6 may be the same or different, and may be each independently hydrogen, isopropyl or benzyl.

At least one of R1 and R2 and at least one of R5 and R6 may be the same or different, and may be each independently an alkyl group of 1 to 20 carbon atoms or an aryl group of 6 to 30 carbon atoms.

At least one of R1 and R2 and at least one of R5 and R6 may be the same or different, and may be each independently isopropyl or benzyl.

R3, R4, R7, R8, R9 and R10 may be the same or different, and may be each independently hydrogen, an alkyl group of 1 to 20 carbon atoms, a cycloalkyl group of 3 to 20 carbon atoms, an aryl group of 6 to 30 carbon atoms, a heteroaryl group of 2 to 30 carbon atoms or the structure represented by Chemical Formula 3, or two or more adjacent substituents among R7 to R10 may be bonded to form a hydrocarbon ring.

R3, R4, R7, R8, R9 and R10 may be the same or different, and may be each independently hydrogen or the structure represented by Chemical Formula 3, or two or more adjacent substituents among R7 to R10 may be bonded to form a hydrocarbon ring.

In case where two or more adjacent substituents among R7 to R10 are bonded to form a hydrocarbon ring, at least one carbon forming the hydrocarbon ring may be substituted with the structure represented by Chemical Formula 3.

At least one of R3 and R4 may be the structure represented by Chemical Formula 3. In addition, at least one of R7 to R10 may be the structure represented by Chemical Formula 3.

The n is a repeating number of the unit in parenthesis and may be an integer of 1 to 30, preferably, 1 to 10. More preferably, 1 to 3.

The A is a nitrogen (N)-containing alkyl group of 1 to 20 carbon atoms, or a nitrogen (N)-containing heteroaryl group of 2 to 30 carbon atoms. Particularly, A may be azide, phthalimide, or amine.

In the present invention, an "adjacent" group may mean a substituent directly coupled with an element at which a corresponding substituent is substituted, a sterically most nearly positioned substituent to the corresponding substituent, or another substituent substituted at an element at which the corresponding substituent is substituted. For example, two substituents substituted at ortho position in a benzene ring, and two substituents substituted at the same carbon in an aliphatic ring may be interpreted as the "adjacent" group.

The alkyl group may be a linear chain or a branched chain, and the carbon number may be 1 to 20, preferably, 1 to 10. More preferably, the carbon number may be 1 to 6. Particular examples of the alkyl group may include methyl, ethyl, propyl, n-propyl, isopropyl, butyl, n-butyl, isobutyl, tert-butyl, sec-butyl, 1-methylbutyl, 1-ethylbutyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethylpropyl, isohexyl, 4-methylhexyl, 5-methylhexyl, benzyl, etc., but is not limited thereto.

The cycloalkyl group may have 3 to 20 carbon atoms, preferably, 3 to 10 carbon atoms. Particular examples of the cycloalkyl group may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, etc., but is not limited thereto.

The aryl group may have 6 to 30 carbon atoms, preferably, 6 to 10 carbon atoms. The aryl group may be a monocyclic aryl group or a polycyclic aryl group. Particular examples of the monocyclic aryl group may include a phenyl group, a biphenyl group, a terphenyl group, etc., and particular examples of the polycyclic aryl group may include a naphthyl group, an anthracenyl group, a phenanthryl group, a pyrenyl group, a perylenyl group, a chrysenyl group, a fluorenyl group, a triphenylene group, etc., but is not limited thereto.

The heteroaryl group is an aromatic ring group including one or more selected from N, O, P, S, Si and Se as heteroatoms, and the carbon number may be 2 to 30, preferably, 2 to 20. Particular examples of the heteroaryl group may include a thiophene group, a furan group, a pyrrole group, an imidazole group, a thiazole group, an oxazole group, an oxadiazole group, a triazole group, a pyridyl group, a pyrimidyl group, a triazine group, a triazole group, an acridyl group, a quinolinyl group, a quinazoline group, a quinoxalinyl group, a phthalazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, etc., but is not limited thereto.

In addition, the alkyl group, the cycloalkyl group, the aryl group, the heteroaryl group or the hydrocarbon ring may be further substituted or unsubstituted with an alkyl group, a cycloalkyl group, an aryl group or a heteroaryl group.

On the surface of the micro-patterned metal layer, one end of the N-heterocyclic carbene compound may be bonded, an in this case, a metal-carbene bond may be formed by a method of chemical vapor deposition (CVD), physical vapor deposition (PVD), thermal evaporation deposition, sputtering deposition, atomic layer deposition (ALD) or chemical-bath deposition (CBD).

Figure 16:
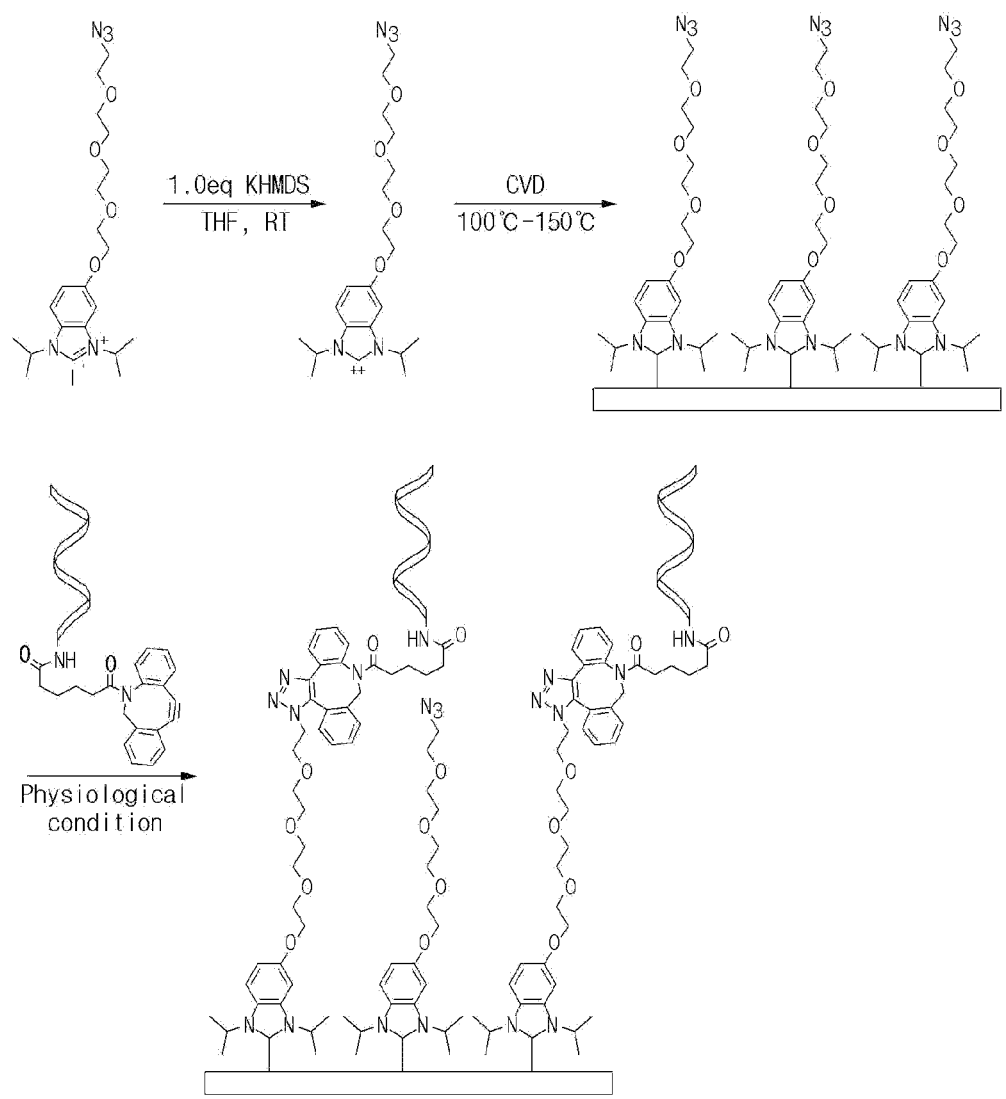
FIG. 16 is a diagram schematically showing a series of processes for immobilizing a primer on a gold (Au) layer using N-heterocyclic carbene compound 4 according to the present invention.
Figure 17:
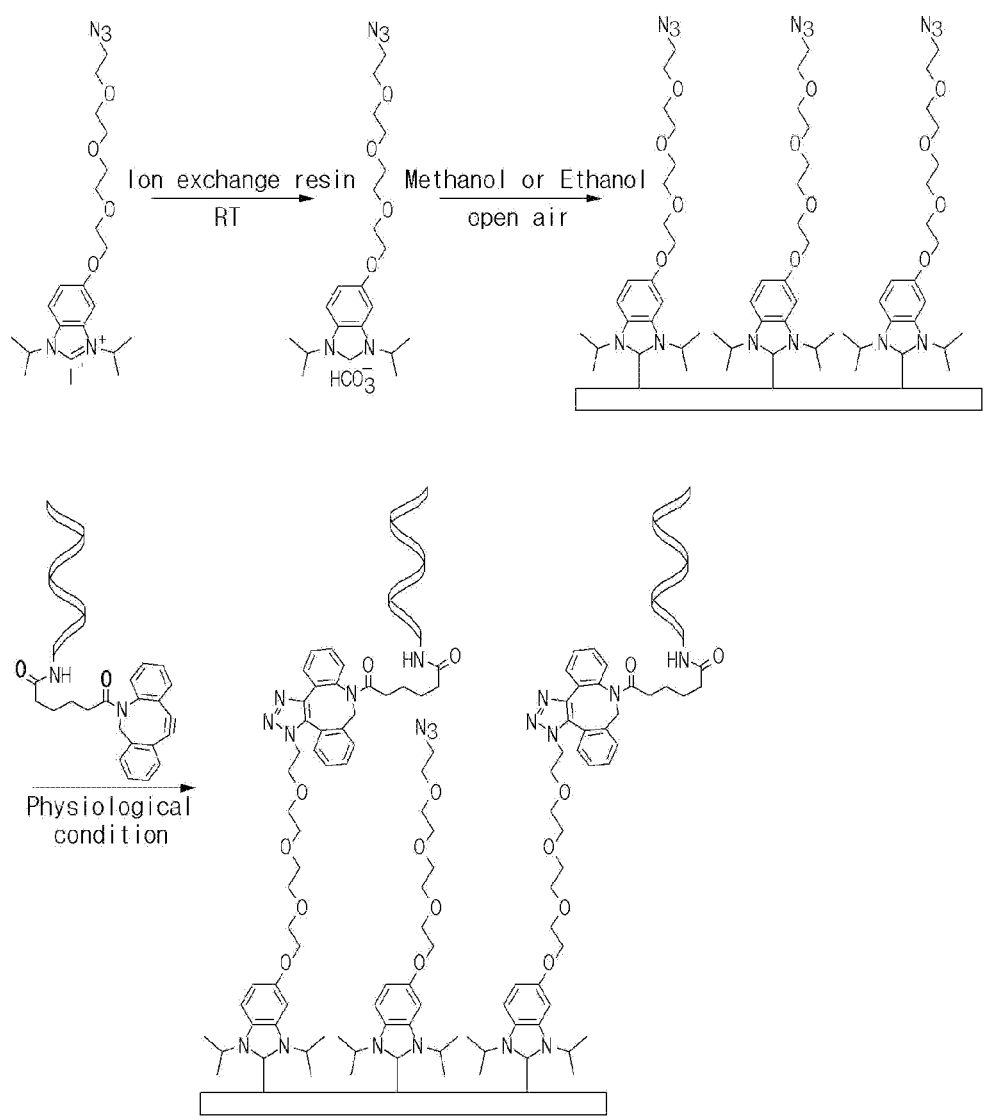
FIG. 17 is a diagram schematically showing a series of processes for immobilizing a primer on a gold (Au) layer using N-heterocyclic carbene compound 4 of the present invention.

According to an embodiment of the present invention, a series of mechanism of bonding one end of the N-heterocyclic carbene compound on the surface of the micro-patterned metal layer by a chemical vapor deposition method is shown in FIG. 16, and a series of mechanism of bonding one end of the N-heterocyclic carbene compound on the surface of the micro-patterned metal layer by a chemical-bath deposition method is shown in FIG. 17.

At the other end of the N-heterocyclic carbene compound, a primer may be bonded and immobilized.

The other end of the N-heterocyclic carbene compound may be functionalized with azide, phthalimide, or amine.

If the other end of the N-heterocyclic carbene compound is functionalized with azide, phthalimide, or amine, a primer may be bonded to the azide, phthalimide, or amine using click reaction as shown in FIGS. 16 and 17. Accordingly, in contrast to the general bonding of the primer with the micro-patterned metal layer by an electrostatic attraction, the primer may be immobilized onto the micro-patterned metal layer through a stronger chemical bond, and if used in the PCR reaction of a solid phase of high temperature, effects of excellent stability, and improved storability and ease of storage may be achieved.

The primer may be a primer of at least one type. The primer of at least one type may mean any one selected from primers which may make complementary bond with different amplification target template DNA (or RNA).

The primer may be a primer of two or more different types. In case where the primer is the primer of two or more different types, any one among a pair of primers which may make complementary bond with a first template DNA (or RNA) to be amplified, and any one among a pair of primers which may make complementary bond with a second template DNA (or RNA) to be amplified. Here, the first template DNA (or RNA) and the second template DNA (or RNA) may mean DNA (or RNA) having different base sequences.

As described above, by immobilizing a primer capable of elongating different template DNA (or RNA) onto the other end of the N-heterocyclic carbene compound which is bonded onto the surface of the micro-patterned metal layer, diverse DNA (or RNA) may be amplified at the same time, and the diagnosis by multiple PCR reactions may be possible in one chamber.

The present invention also provides a method for manufacturing a substrate for nucleic acid amplification, including: forming a micro-patterned metal layer on a transparent matrix; introducing one end of an N-heterocyclic carbene compound onto the surface of the micro-patterned metal layer; and immobilizing a primer on the other end of the N-heterocyclic carbene compound.

FIG. 1 is a diagram schematically showing a series of a process of light-based PCR reaction using the substrate for nucleic acid amplification of the present invention.

The schematic explanation on a process for performing the light energy-based PCR reaction using the substrate for nucleic acid amplification of the present invention is as follows, but the PCR reaction is not limited only to the method described below.

A PCR specimen including amplification target template DNA, dNTP, Taq polymerase, etc., is prepared. Two types of primers (forward primer, reverse primer) making complementary bond with the template DNA are prepared. A portion of the forward primer is immobilized by bonding with the end of the transparent matrix/micro-patterned metal layer/N-heterocyclic carbene compound linker, which is the substrate for nucleic acid amplification of the present invention, and the remaining forward primer and reverse primer are included in the PCR reaction specimen. Then, light energy is irradiated by a light source (LED, etc.) positioned under the transparent matrix, and PCR reaction is performed.

In the conventional PCR substrate in which a primer is immobilized on the surface of a micro-patterned metal layer by a metal-sulfur bond using a thiol (—SH) group as a linker, there are problems in that the metal-sulfur bond is liable at high temperature (about 90° C. or more), and the linker is easily separated. Accordingly, the application thereof to light energy-based PCR by which the surface temperature by the light energy is elevated to 500° C., is impossible, and the application thereof is possible only to a PCR machine using thermal energy converted from electrical energy.

However, in case of performing PCR reaction using the substrate for nucleic acid amplification of the present invention, the N-heterocyclic carbene compound is attached onto the surface (solid phase) of the micro-patterned metal layer as a linker, and then the primer is immobilized, and accordingly, stability at high temperature is better in contrast to a linker by the bonding of the metal and thiol (—SH), and thus, the application to a PCR machine using thermal energy converted from light energy is possible, prompt temperature control of the micro-patterned metal layer by the irradiation of light energy is possible due to the above-described vortex phenomenon, and the PCR reaction may be completed within a very short time with about 8 minutes to 10 minutes for performing 40 cycles for the PCR reaction.

In addition, as described above, since the amplification of diverse nucleic acids at the same time is possible by using the primer of at least one type (or a primer of different two types), there are advantages in that multiple PCR reactions may be performed and more precise diagnosis may be served. In addition, different from PCR which is performed only in a liquid phase, the substrate for nucleic acid amplification may be easily recovered after the PCR reaction, and the storage of the primer is easy, and the regeneration thereof is possible.

Hereinafter, the present invention will be explained in more detail referring to preferred embodiments.

However, these embodiments are for explaining the present invention more particularly, and the scope of the present invention is not limited thereto.

PREPARATION EXAMPLE

Preparation Example 1

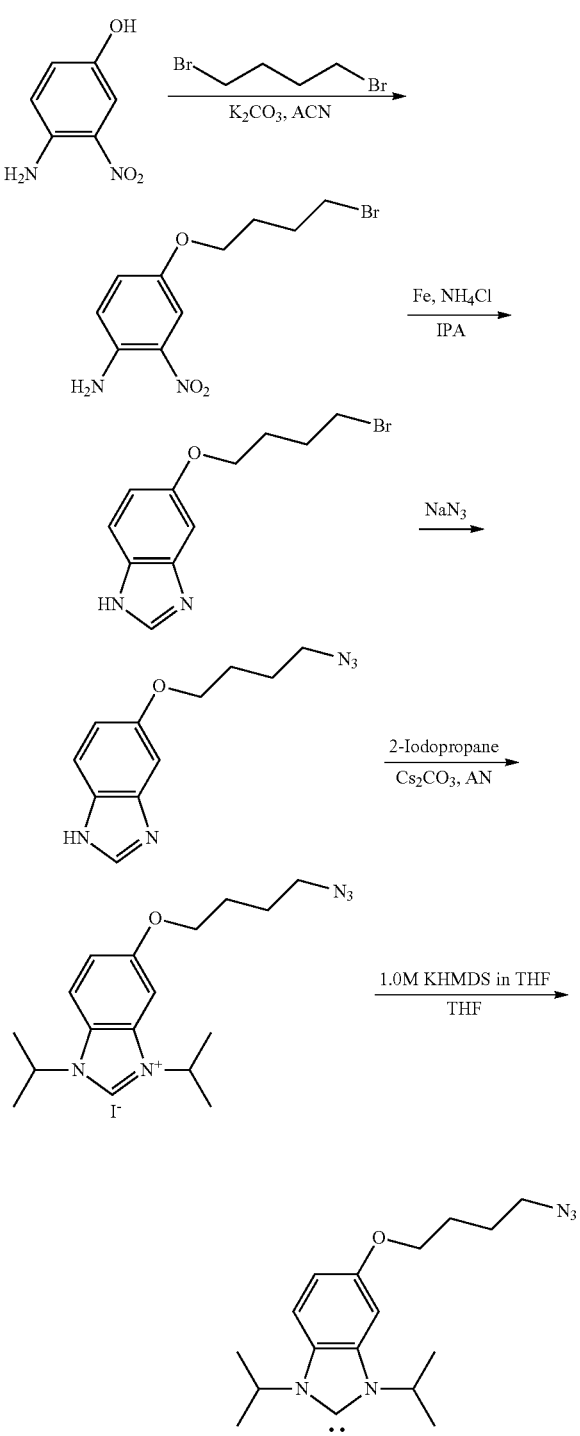

According to the reaction above, N-heterocyclic carbene compound 1 was prepared.

Figure 7:
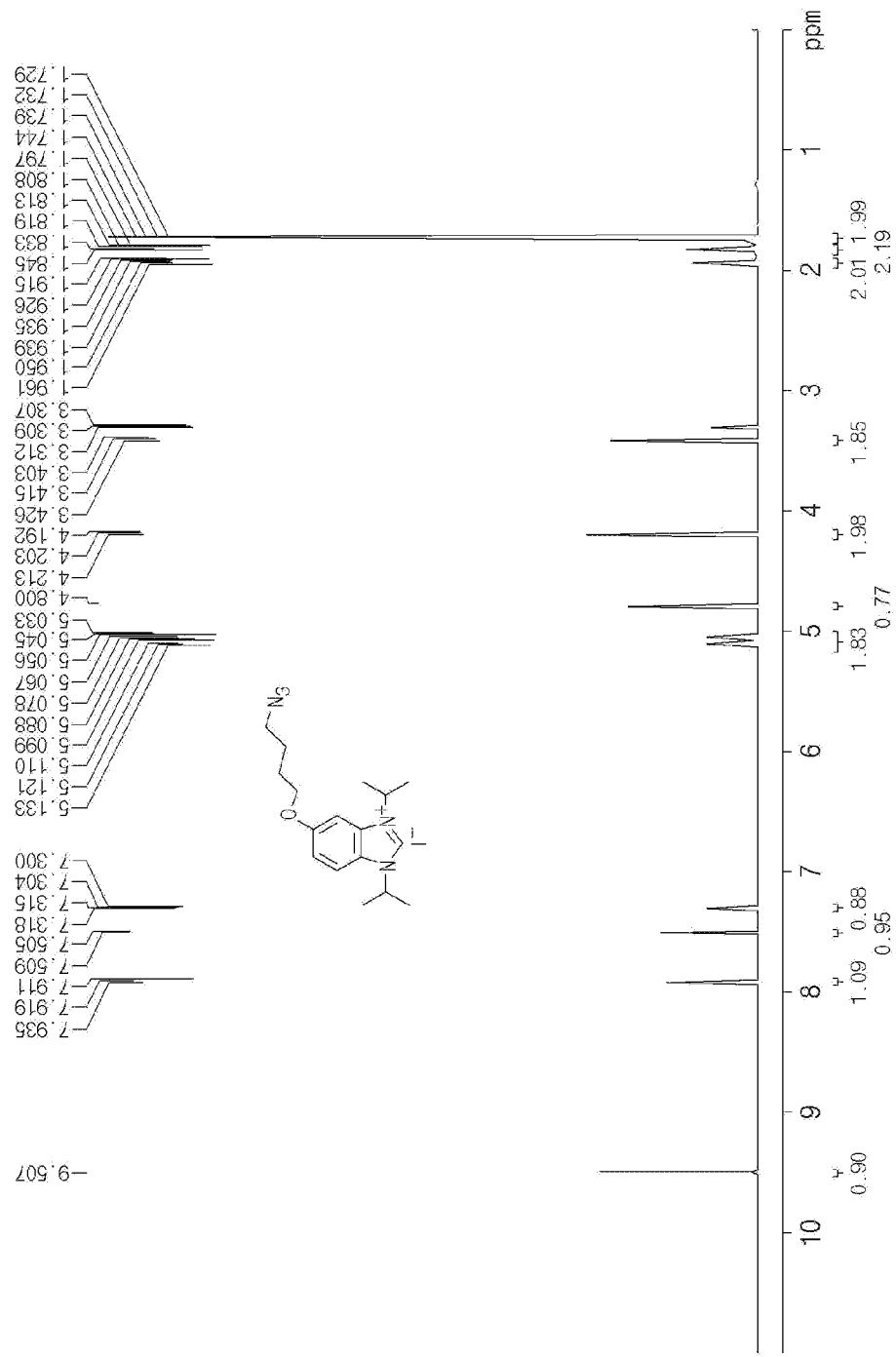
FIG. 7 is a diagram showing $^1$H-NMR spectrum of N-heterocyclic carbene compound 1 prepared according to Preparation Example 1 of the present invention.

In FIG. 7, the $^1$H-NMR spectrum of N-heterocyclic carbene compound 1 is shown.

Figure 8:
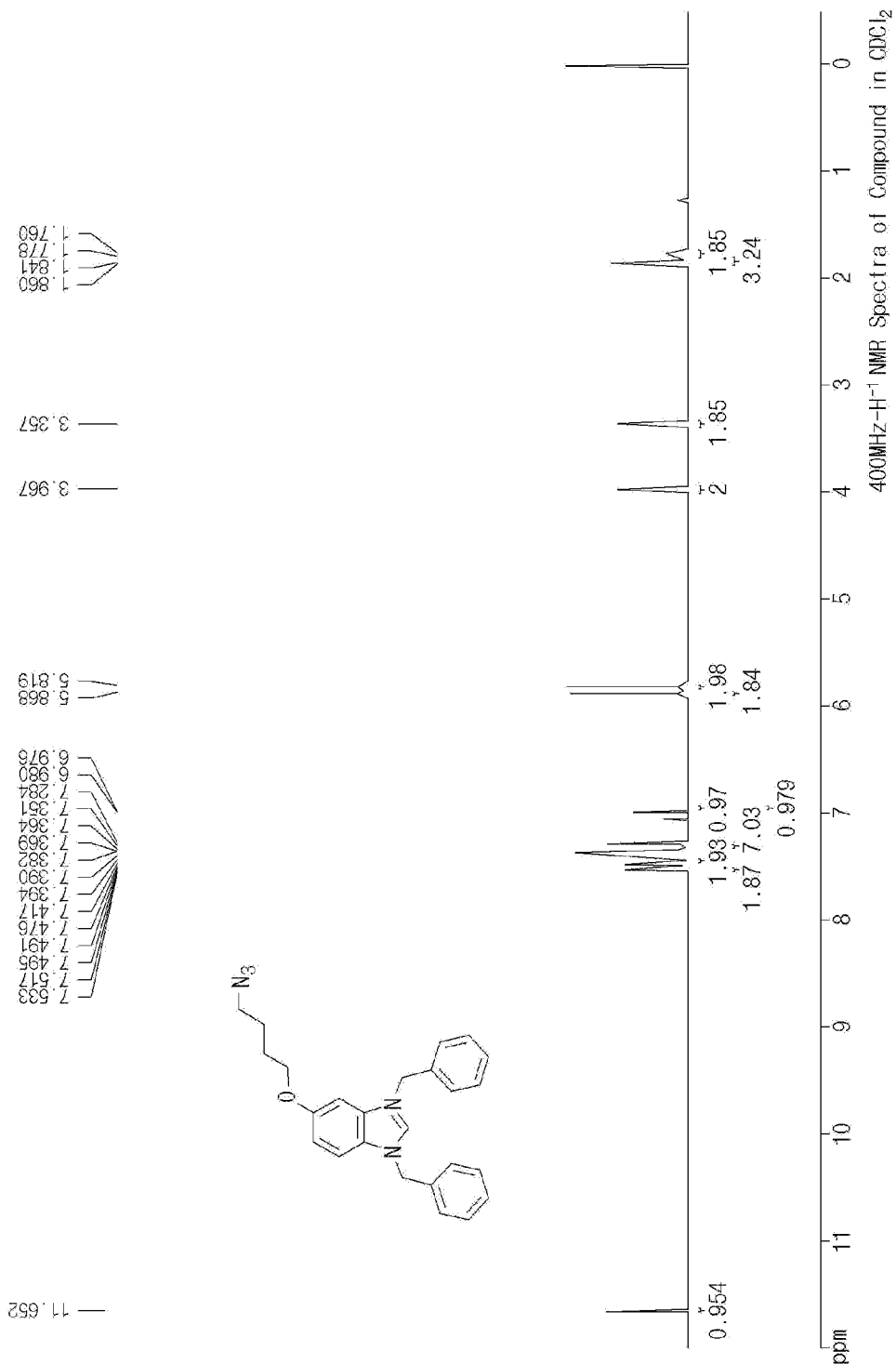
FIG. 8 is a diagram showing $^1$H-NMR spectrum of N-heterocyclic carbene compound 2 prepared according to Preparation Example 2 of the present invention.
Figure 9:
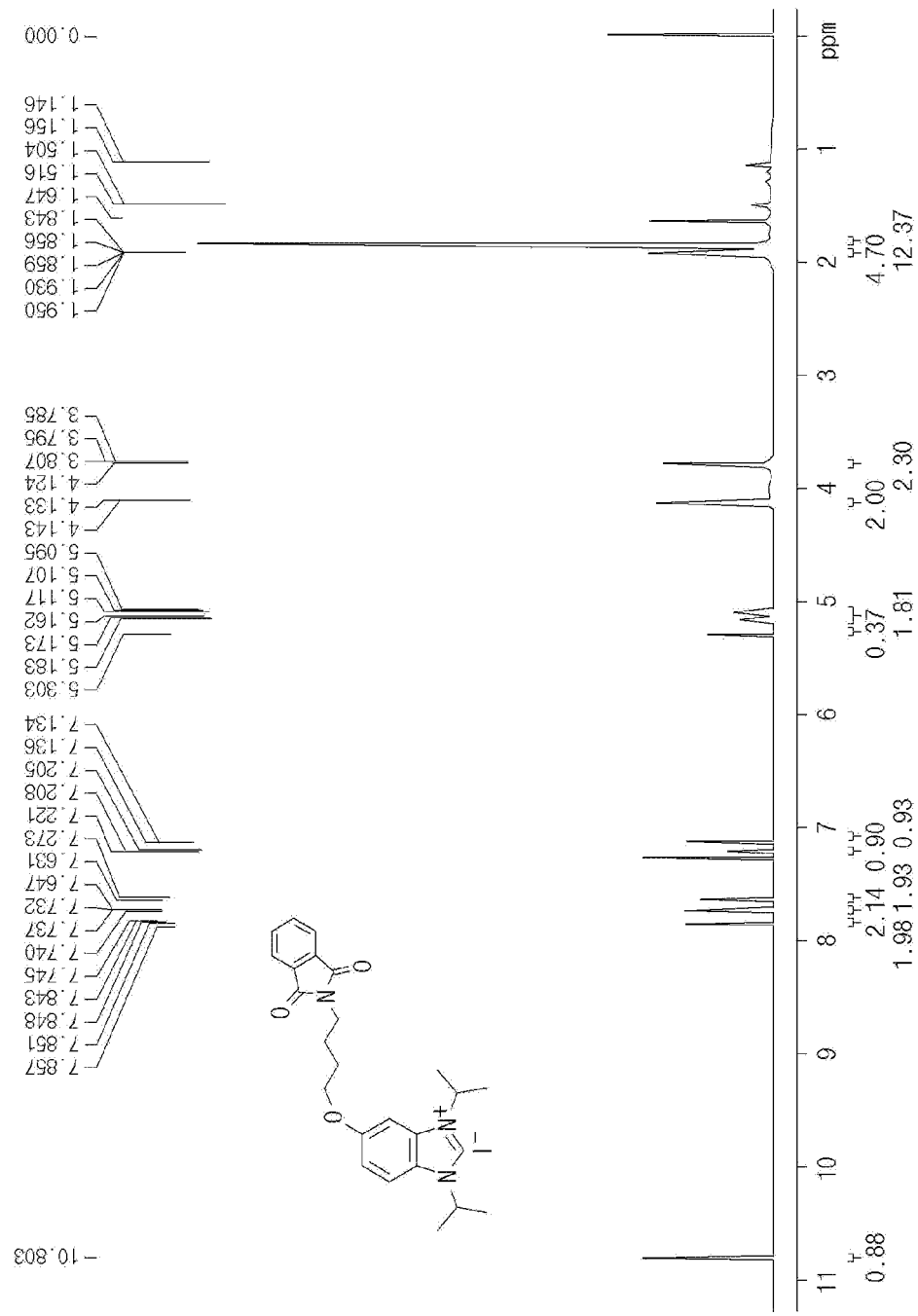
FIG. 9 is a diagram showing $^1$H-NMR spectrum of N-heterocyclic carbene compound 3 prepared according to Preparation Example 3 of the present invention.

Preparation Example 2
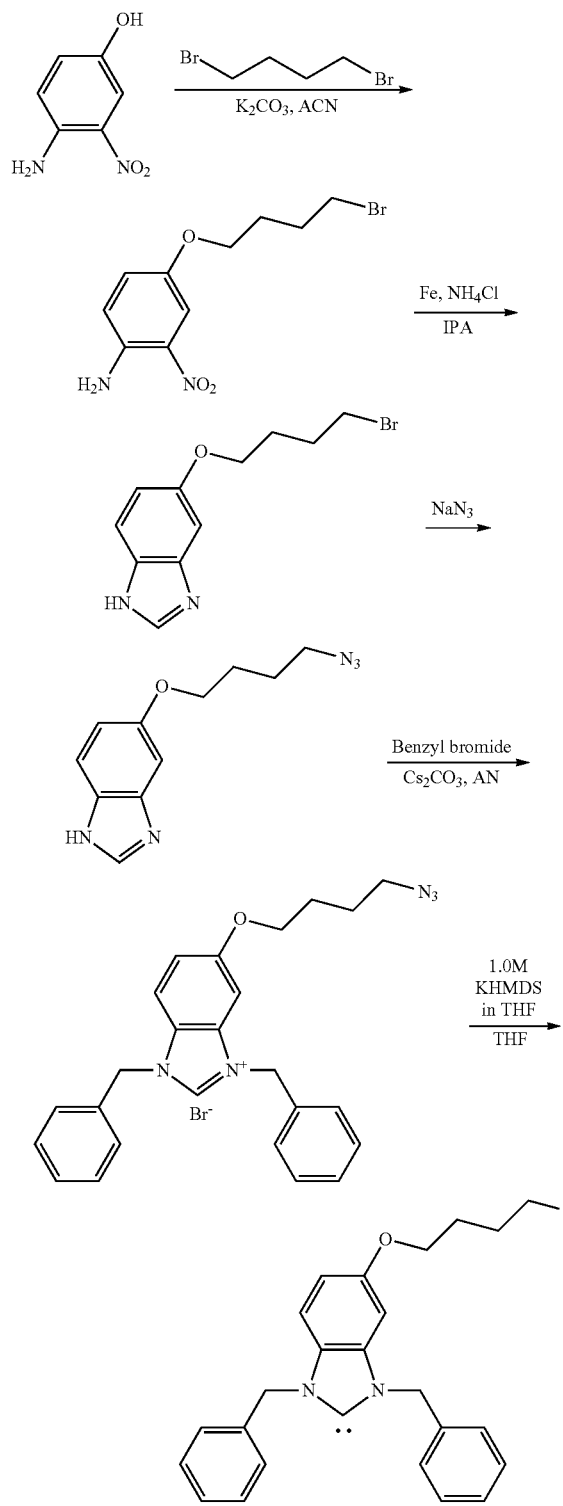
According to the reaction above, N-heterocyclic carbene compound 2 was prepared.
In FIG. 8, the $^1$H-NMR spectrum of N-heterocyclic carbene compound 2 is shown.
Preparation Example 3
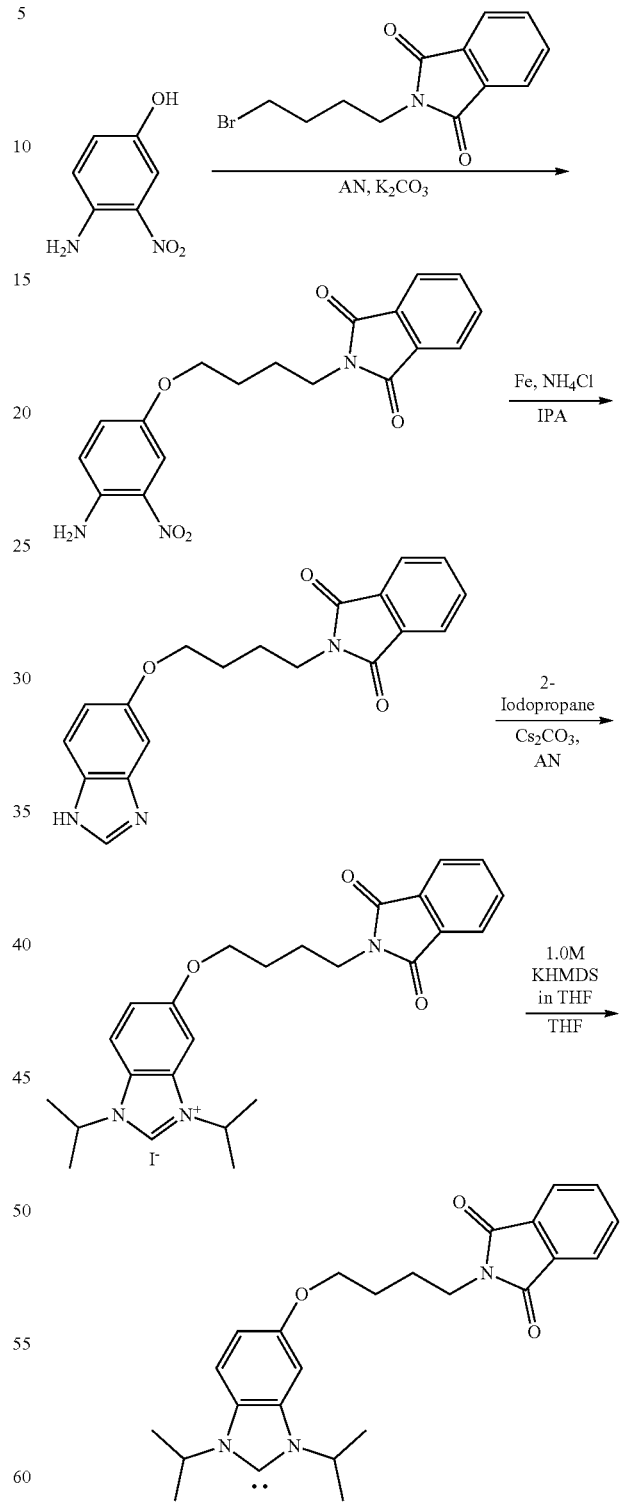
According to the reaction above, N-heterocyclic carbene compound 3 was prepared.
In FIG. 9, the $^1$H-NMR spectrum of N-heterocyclic carbene compound 3 is shown.

Figure 10:
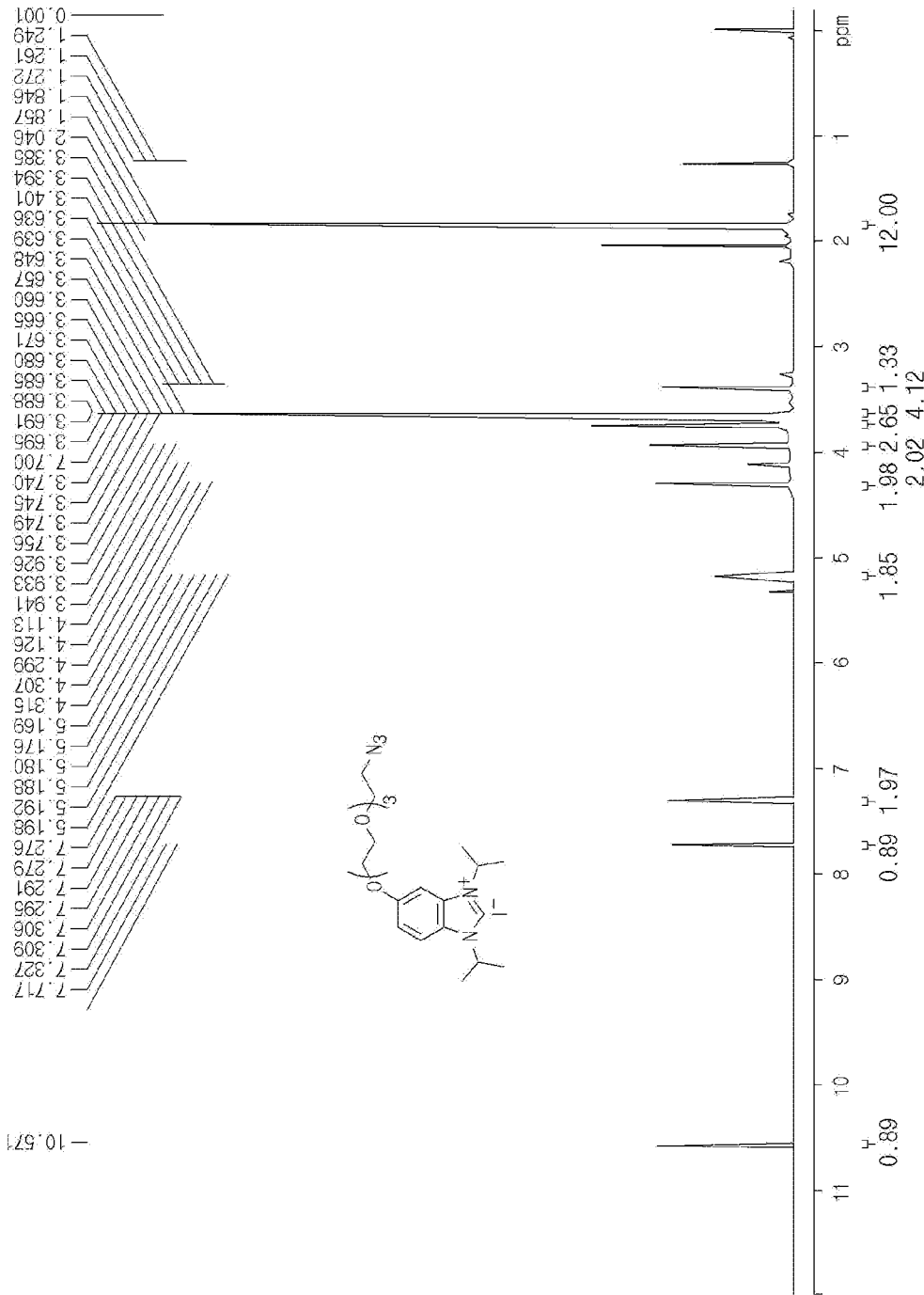
FIG. 10 is a diagram showing $^1$H-NMR spectrum of N-heterocyclic carbene compound 4 prepared according to Preparation Example 4 of the present invention.

Preparation Example 4
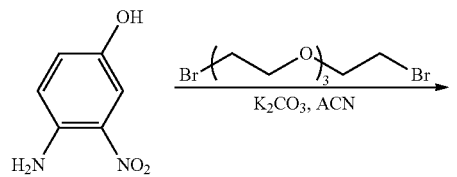
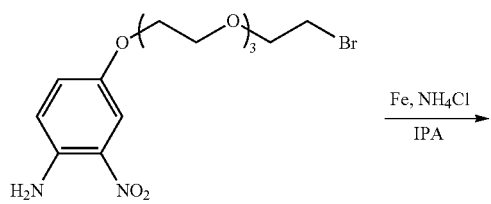
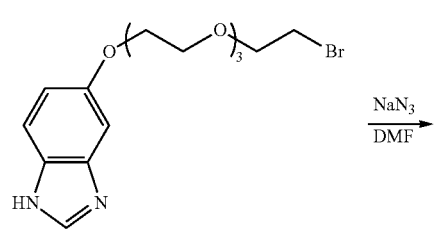
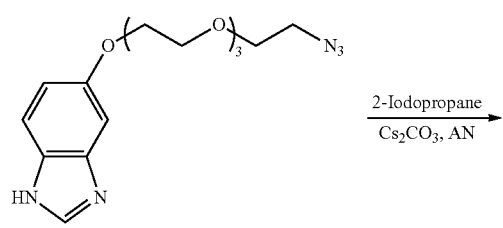
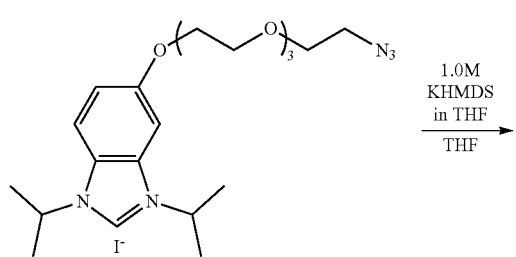
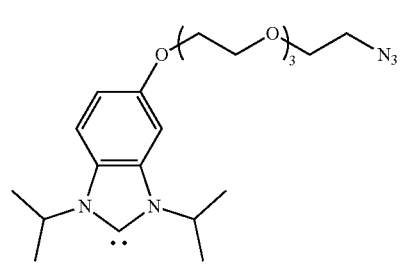
According to the reaction above, N-heterocyclic carbene compound 4 was prepared.
In FIG. 10, the ¹H-NMR spectrum of N-heterocyclic carbene compound 4 is shown.
Preparation Example 5
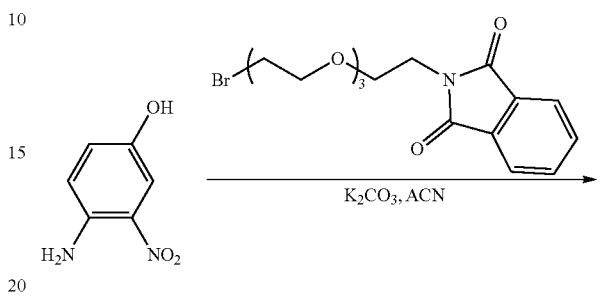
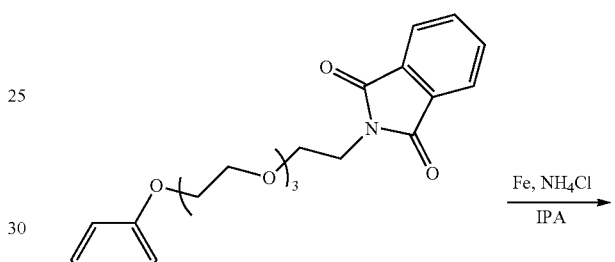
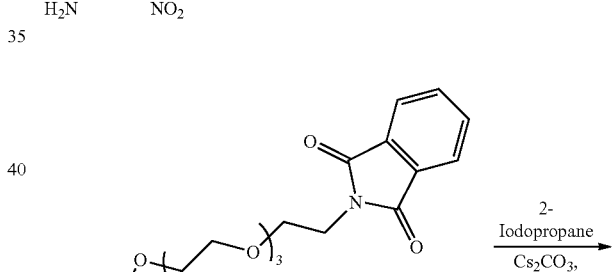
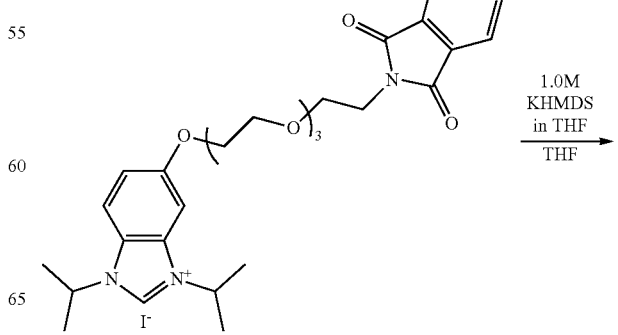

-continued

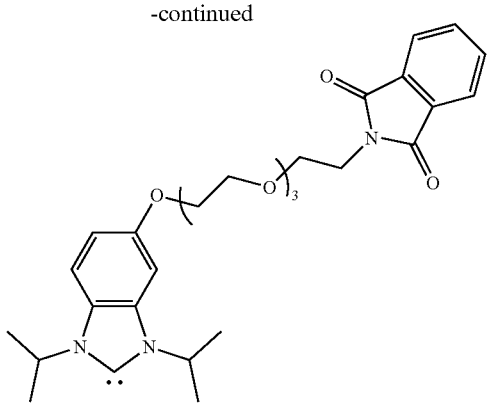

According to the reaction above, N-heterocyclic carbene compound 5 was prepared.

Figure 11:
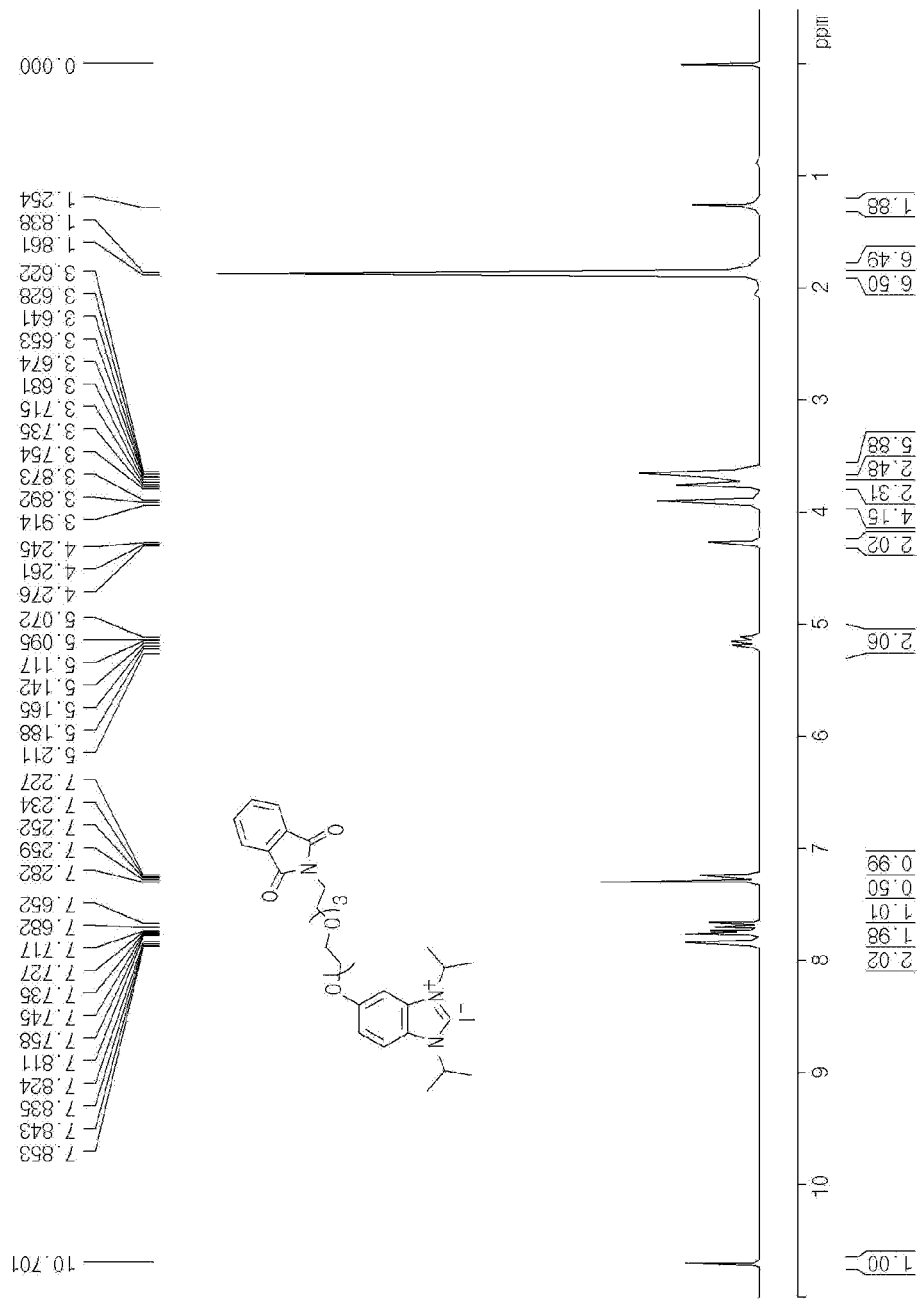
FIG. 11 is a diagram showing $^1$H-NMR spectrum of N-heterocyclic carbene compound 5 prepared according to Preparation Example 5 of the present invention.

In FIG. 11, the $^1$H-NMR spectrum of N-heterocyclic carbene compound 5 is shown.

EXPERIMENTAL EXAMPLE

Figure 18:
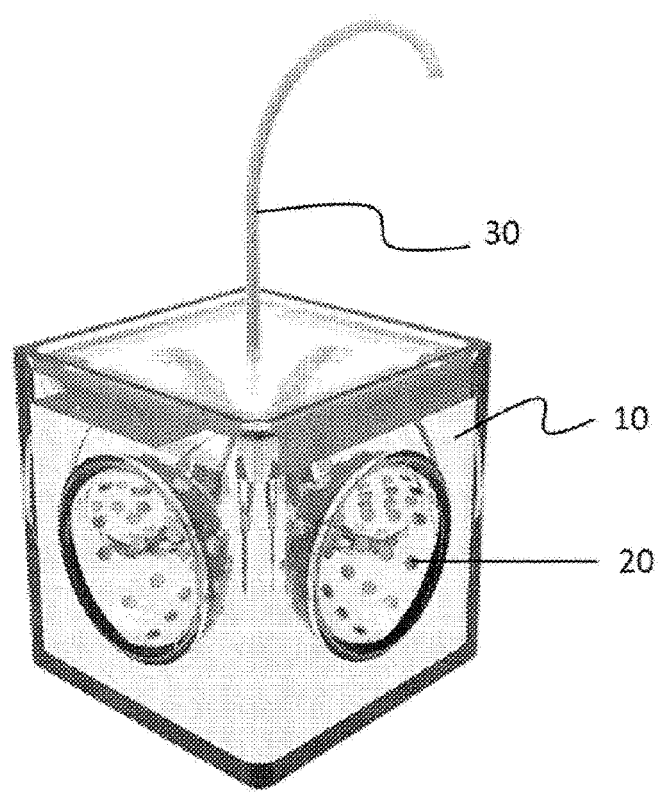
FIG. 18 is a diagram showing a transparent matrix and a metal layer formed on the transparent matrix according to an embodiment of the present invention.

On a micro-patterned gold (Au) layer into a honeycomb pattern, a primer (Geno Tech Corp.) with a fluorescence material (Cy5) attached thereto was immobilized using N-heterocyclic carbene compound 1 prepared in Preparation Example 1 as a linker, and observed results using a fluorescence microscope are shown in FIG. 18.

According to FIG. 18, it was confirmed that the primer was bonded well with the N-heterocyclic carbene compound.

Example

Example 1

As template DNA, a lung cancer cell line, cDNA of A549 was used, and a PCR reactant of a liquid phase including dNTP, Taq polymerase, a reverse primer below and a forward primer below was prepared.

Figure 2:
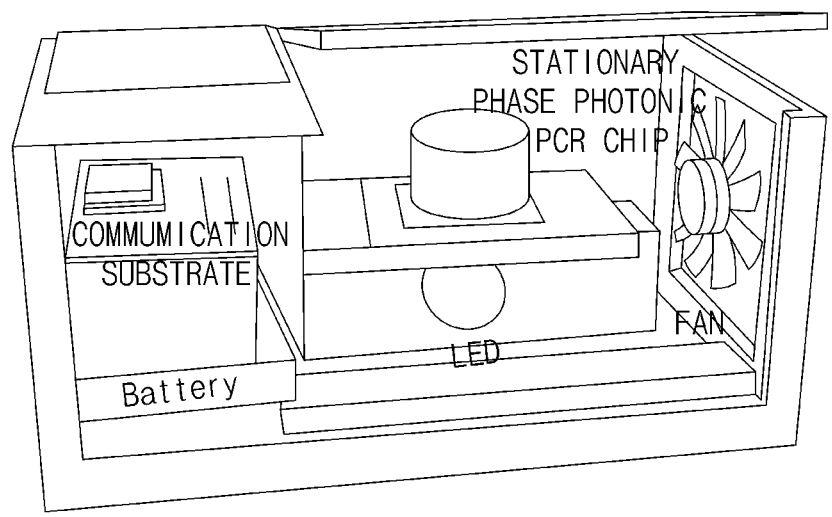
FIG. 2 is a diagram schematically showing a light-based PCR machine on a solid phase using the substrate for nucleic acid amplification of the present invention.
Figure 12:
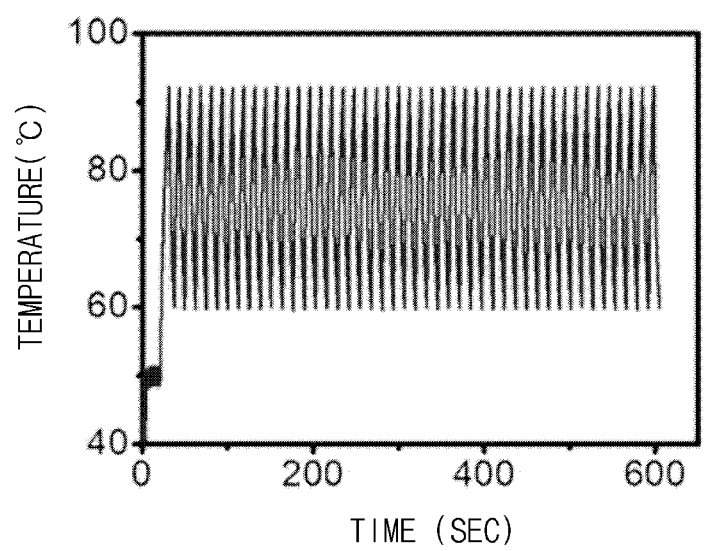
FIG. 12 is a diagram showing time required for performing 40 cycles of PCR reaction according to Examples 1 and 2 of the present invention.
Figure 28:
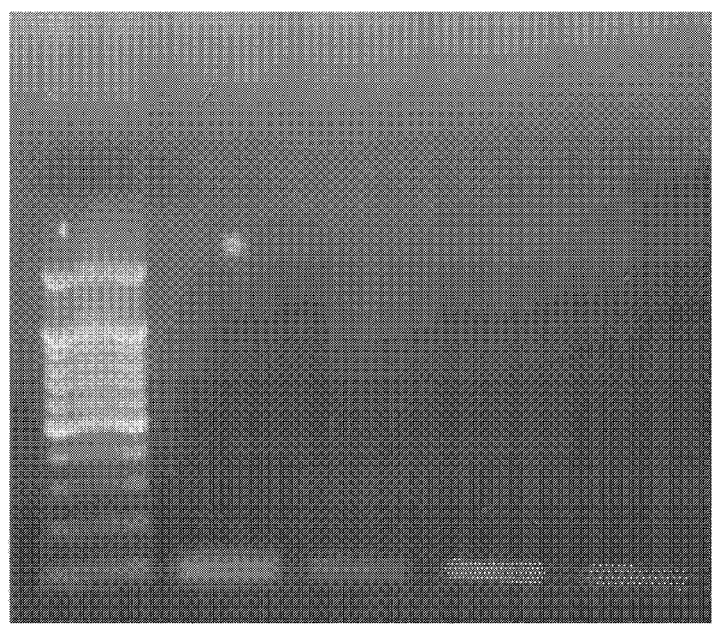
FIG. 28 is a diagram showing electrophoretic results confirming the completion of PCR reaction after performing PCR reaction according to Example 1 of the present invention.

On a planar type glass matrix, a micro-patterned gold (Au) layer into a honeycomb pattern as shown in FIG. 3 and FIG. 4 was prepared. By using N-heterocyclic carbene compound 4 prepared in Preparation Example 4, a forward primer below was immobilized on the surface of a micro-patterned gold (Au) layer. The substrate on which the forward primer was immobilized was put in a PCR reactant of a liquid phase, which included a relatively small amount of the forward primer, and by using the machine of FIG. 2, PCR reaction of 40 cycles was performed. The time required for performing 40 cycles of the PCR reaction is shown in FIG. 12, and 5 μl of the PCR reaction resultant was loaded on 1 wt % of an agarose gel, and electrophoresis (Mupid 2Plus of GenomicBase Co.) was performed under conditions of 100 V and 20 minutes. In comparison to the conventional RT PCR reaction resultant, the completion of the PCR reaction using the PCR substrate of the present invention was confirmed through FIG. 28.

[Primer Immobilized onto Substrate of Solid Phase]
Forward primer: 5'-Amino(C12)-TTTTTTTTTTGACC-CAATCATGAGCACTGCTTT-3'

[Primer in PCR Reactant of Liquid Phase]
Forward primer: 5'-GACCCAATCATGAGCACTG-3'
Reverse primer: 5'-TGAAGCGACCCTCTGATG-3'

Example 2

In Example 1, PCR reaction was performed by the same method in Example 1 except for using a mutated lung cancer cell line, cDNA of NCI-H-1975 instead of the lung cancer cell line, cDNA of A549, as the template DNA.

Example 3

Figure 19:
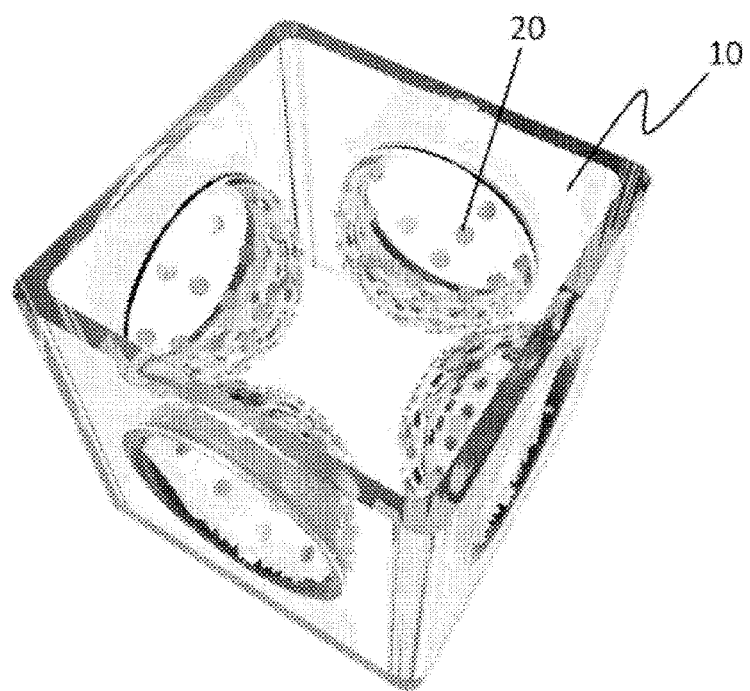
FIG. 19 is a diagram showing a transparent matrix and a metal layer formed on the transparent matrix according to an embodiment of the present invention.
Figure 20:
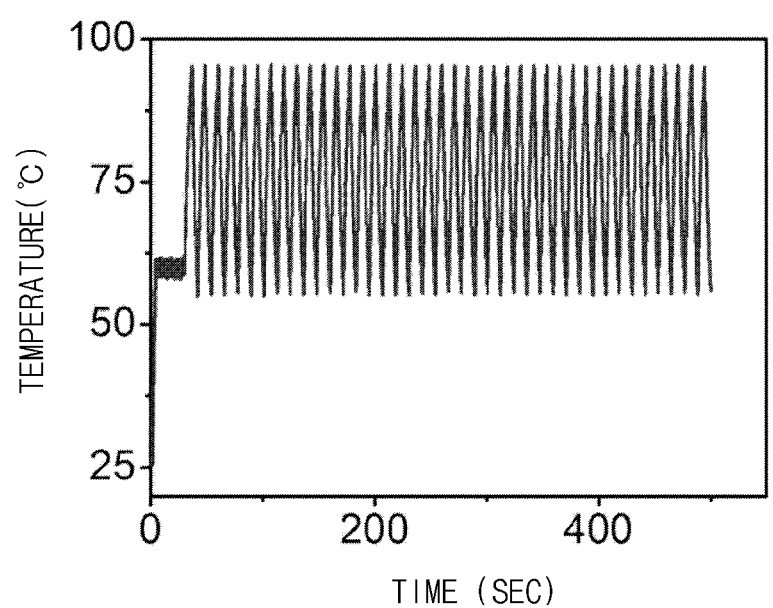
FIG. 20 is a diagram showing time required for performing 40 cycles of PCR reaction according to Example 3 of the present invention.
Figure 21:
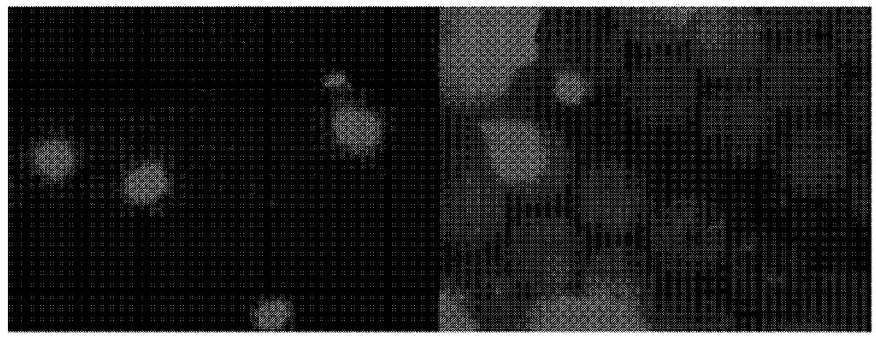
FIG. 21 is a diagram showing observed results using a fluorescence microscope according to the Experimental Example of the present invention.
Figure 22:
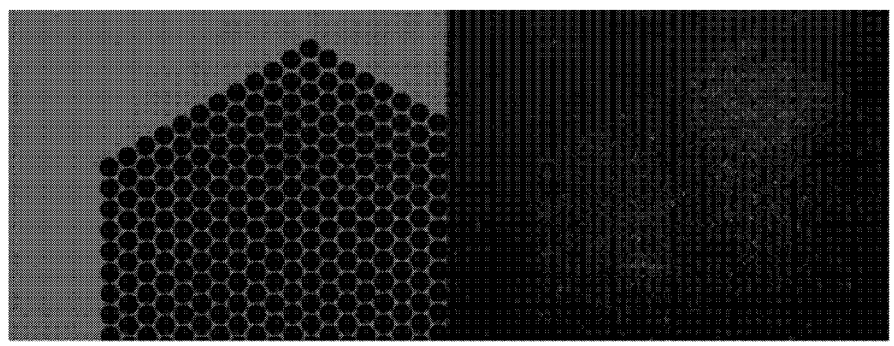
FIG. 22 is a diagram showing detection results using a fluorescence material PCR reaction after performing according to Example 1 of the present invention.
Figure 23:
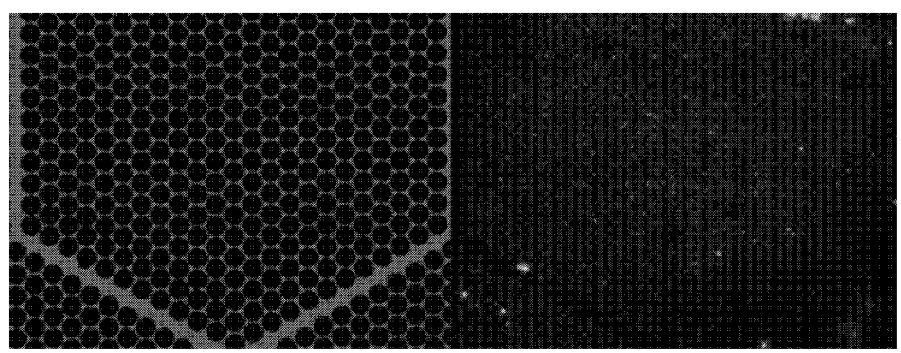
FIG. 23 is a diagram showing detection results using a fluorescence material performing PCR reaction according to Example 2 of the present invention.

In Example 1, PCR reaction was performed by the same method in Example 1 except for using a hexahedral glass matrix as in FIG. 18 and FIG. 19 instead of the planar type glass matrix. The time required for performing 40 cycles of the PCR reaction is shown in FIG. 20.

Comparative Example 1

PCR reaction was performed by the same method in Example 1 except for performing the PCR reaction without the template DNA.

The PCR products of Examples 1 to 3 and Comparative Example 1 were treated with SYBR (chelating dye), fluorescence was measured, and the results are shown in FIG. 22 to FIG. 25.

Figure 25:
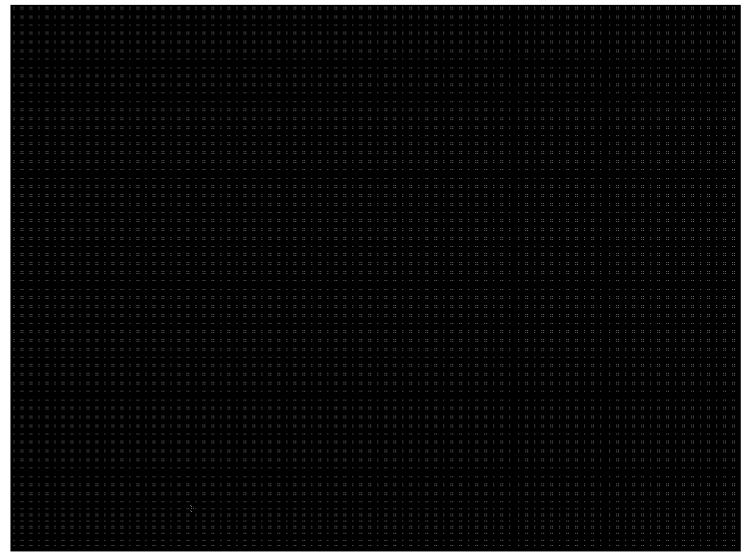
FIG. 25 is a diagram showing detection results using a fluorescence material after performing PCR reaction according to Comparative Example 1 of the present invention.

According to FIG. 25, in Comparative Example 1 in which the template DNA was not used, and the PCR reaction was not performed, fluorescence was not generated. In contrast, according to FIG. 12, FIG. 22 and FIG. 23, in Examples 1 and 2 which used the cDNA of A549 cell line and NCI-H-1975 cell line as the templates, sufficient PCR products were produced within a short time of about 10 minutes in both Examples 1 and 2, and the generation of fluorescence was confirmed.

Figure 24:
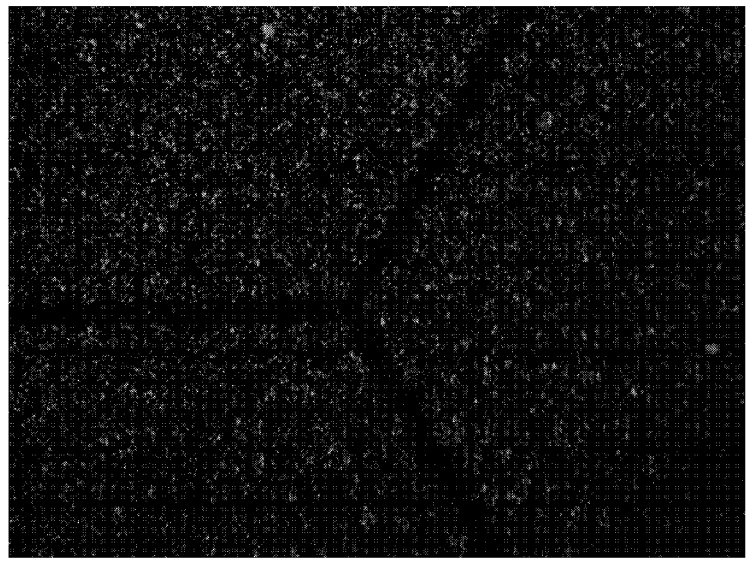
FIG. 24 is a diagram showing detection results using a fluorescence material after performing PCR reaction according to Example 3 of the present invention.

In addition, according to FIG. 20 and FIG. 24, in Example 3 which used the hexahedral glass matrix, a sufficient PCR product was produced within about 8 to minutes, and the generation of fluorescence was confirmed.

In the above, only given embodiments of the present invention have been explained in detail, but various variations and modifications are apparent to a person in this art within the technical scope of the present invention, and such variations and modifications are certainly included in the appended claims.

The invention claimed is:

1. A substrate for nucleic acid amplification, used in light-based polymerase chain reaction (PCR) using thermal energy produced by the irradiation of light energy from light sources, comprising:
   a transparent matrix;
   a micro-patterned metal layer formed on the transparent matrix;
   an N-heterocyclic carbene compound having one end bonded to the surface of the micro-patterned metal layer; and
   at least one pair of primers immobilized on the other end of the N-heterocyclic carbene compound,
   wherein the N-heterocyclic carbene compound is represented by the following Chemical Formula 1 or 2:

[Chemical Formula 1]

[Chemical Formula 2]

in Chemical Formulae 1 and 2,
R1, R2, R5 and R6 are the same or different, and are each independently hydrogen, an alkyl group of 1 to 20 carbon atoms, a cycloalkyl group of 3 to 20 carbon atoms, an aryl group of 6 to 30 carbon atoms or a heteroaryl group of 2 to 30 carbon atoms, R3, R4, R7, R8, R9 and R10 are the same or different, and are each independently, hydrogen, an alkyl group of 1 to 20 carbon atoms, a cycloalkyl group of 3 to 20 carbon atoms, an aryl group of 6 to 30 carbon atoms, a heteroaryl group of 2 to 30 carbon atoms or a structure represented by the following Chemical Formula 3, where adjacent two or more substituents among R7 to R10 are bonded to form a hydrocarbon ring, at least one of R3 and R4 is the structure represented by the following Chemical Formula 3, and at least one of R7 to R10 is substituted with the structure represented by the following Chemical Formula 3, or in case where adjacent two or more substituents among R7 to R10 are bonded to form a hydrocarbon ring, at least one of carbon atoms forming the hydrocarbon ring is substituted with the structure represented by the following Chemical Formula 3:

[Chemical Formula 3]

$$-\text{O}-(\text{CH}_2-\text{CH}_2-\text{O})_n-\text{A}$$

in Chemical Formula 3,
n is a repeating number of a unit in parenthesis and an integer of 1 to 30, and
A is a nitrogen (N)-containing alkyl group of 1 to 20 carbon atoms or a nitrogen (N)-containing heteroaryl group of 2 to 30 carbon atoms.

2. The substrate for nucleic acid amplification according to claim 1, wherein the micro-pattern is a honeycomb pattern.

3. The substrate for nucleic acid amplification according to claim 1, wherein the transparent matrix comprises at least one matrix selected from a two-dimensional matrix of a planar type; at least one three-dimensional matrix selected from a spherical type, a hemispherical type, a polyhedral type, a polyprism type, and a cylindrical type; and a mixture type thereof.

4. The substrate for nucleic acid amplification according to claim 1, wherein the metal layer further comprises a metal mesh.

5. The substrate for nucleic acid amplification according to claim 1, wherein the metal layer comprises gold (Au).

6. The substrate for nucleic acid amplification according to claim 1, wherein the other end of the N-heterocyclic carbene compound is functionalized with azide, phthalimide, or amine prior to the immobilization of the at least one pair of primers.

7. The substrate for nucleic acid amplification according to claim 1, wherein the at least one pair of primers complementary binds to at least one template nucleic acid.

8. A method for manufacturing a substrate for nucleic acid amplification, wherein the substrate is used in light-based polymerase chain reaction (PCR) using thermal energy produced by the irradiation of light energy from light sources, the method comprising:
forming a micro-patterned metal layer on a transparent matrix;
introducing one end of an N-heterocyclic carbene compound onto the surface of the micro-patterned metal layer; and
immobilizing at least one pair of primers on the other end of the N-heterocyclic carbene compound,
wherein the N-heterocyclic carbene compound is represented by the following Chemical Formula 1 or 2:

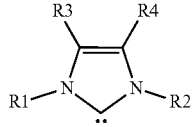
[Chemical Formula 1]

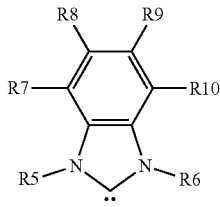
[Chemical Formula 2]

in Chemical Formulae 1 and 2,
R1, R2, R5 and R6 are the same or different, and are each independently hydrogen, an alkyl group of 1 to 20 carbon atoms, a cycloalkyl group of 3 to 20 carbon atoms, an aryl group of 6 to 30 carbon atoms or a heteroaryl group of 2 to 30 carbon atoms,
R3, R4, R7, R8, R9 and R10 are the same or different, and are each independently hydrogen, an alkyl group of 1 to 20 carbon atoms, a cycloalkyl group of 3 to 20 carbon atoms, an aryl group of 6 to 30 carbon atoms, a heteroaryl group of 2 to 30 carbon atoms or a structure represented by the following Chemical Formula 3,
where adjacent two or more substituents among R7 to R10 are bonded to form a hydrocarbon ring,
at least one of R3 and R4 is the structure represented by the following Chemical Formula 3, and
at least one of R7 to R10 is substituted with the structure represented by the following Chemical Formula 3, or in case where adjacent two or more substituents among R7 to R10 are bonded to form a hydrocarbon ring, at least one of carbon atoms forming the hydrocarbon ring is substituted with the structure represented by the following Chemical Formula 3:

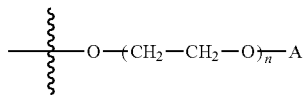
[Chemical Formula 3]

in Chemical Formula 3,
n is a repeating number of a unit in parenthesis and an integer of 1 to 30, and
A is a nitrogen (N)-containing alkyl group of 1 to 20 carbon atoms or a nitrogen (N)-containing heteroaryl group of 2 to 30 carbon atoms.

9. The method for manufacturing a substrate for nucleic acid amplification according to claim 8, wherein the micropattern is a honeycomb pattern.

10. The method for manufacturing a substrate for nucleic acid amplification according to claim 8, wherein the transparent matrix comprises at least one matrix selected from a two-dimensional matrix of a planar type; at least one three-dimensional matrix selected from a spherical type, a hemispherical type, a polyhedral type, a polyprism type, and a cylindrical type; and a mixture type thereof.

11. The method for manufacturing a substrate for nucleic acid amplification according to claim 8, wherein the metal layer further comprises a metal mesh.

12. The method for manufacturing a substrate for nucleic acid amplification according to claim 8, wherein the one end of the N-heterocyclic carbene compound is introduced onto the surface of the micro-patterned metal layer through a metal-carbene bond.

13. The method for manufacturing a substrate for nucleic acid amplification according to claim 8, wherein the other end of the N-heterocyclic carbene compound is functionalized with azide, phthalimide, or amine prior to the immobilization of the at least one pair of primers.

14. The method for manufacturing a substrate for nucleic acid amplification according to claim 8, wherein the primer is immobilized on the other end of the N-heterocyclic carbene compound by click reaction.

15. The method for manufacturing a substrate for nucleic acid amplification according to claim 8, wherein the metal layer comprises gold (Au).

16. The method for manufacturing a substrate for nucleic acid amplification according to claim 8, wherein the at least one pair of primers complementary binds to at least one template nucleic acid.

* * * * *

SEQUENCE LISTING

<160> NUMBER OF SEQ ID NOS: 3

<210> SEQ ID NO 1
<211> LENGTH: 33
<212> TYPE: DNA
<213> ORGANISM: Artificial Sequence

```
<220> FEATURE:
<223> OTHER INFORMATION: Forward Primer immobilized onto substrate of
      solid phase

<400> SEQUENCE: 1
tttttttttt gacccaatca tgagcactgc ttt                                33

<210> SEQ ID NO 2
<211> LENGTH: 19
<212> TYPE: DNA
<213> ORGANISM: Artificial Sequence
<220> FEATURE:
<223> OTHER INFORMATION: Forward Primer in PCR reactant of liquid phase

<400> SEQUENCE: 2
gacccaatca tgagcactg                                                19

<210> SEQ ID NO 3
<211> LENGTH: 18
<212> TYPE: DNA
<213> ORGANISM: Artificial Sequence
<220> FEATURE:
<223> OTHER INFORMATION: Reverse Primer in PCR reactant of liquid phase

<400> SEQUENCE: 3
tgaagcgacc ctctgatg                                                 18
```